US011612332B2

(12) United States Patent
Chetham

(10) Patent No.: US 11,612,332 B2
(45) Date of Patent: Mar. 28, 2023

(54) HYDRATION STATUS MONITORING

(71) Applicant: Impedimed Limited, Pinkenba (AU)

(72) Inventor: Scott Chetham, Del Mar, CA (US)

(73) Assignee: IMPEDIMED LIMITED, Pinkenba (AU)

(*) Notice: Subject to any disclaimer, the term of this patent is extended or adjusted under 35 U.S.C. 154(b) by 0 days.

(21) Appl. No.: 15/623,099

(22) Filed: Jun. 14, 2017

(65) Prior Publication Data

US 2017/0340238 A1    Nov. 30, 2017

Related U.S. Application Data

(63) Continuation of application No. 12/090,078, filed as application No. PCT/AU2006/001491 on Oct. 10, 2006, now Pat. No. 9,724,012.

(30) Foreign Application Priority Data

Oct. 11, 2005    (AU) .................. 2005905603

(51) Int. Cl.
A61B 5/0537   (2021.01)
A61B 5/00     (2006.01)
G16H 50/30    (2018.01)

(52) U.S. Cl.
CPC .......... *A61B 5/0537* (2013.01); *A61B 5/4875* (2013.01); *A61B 5/4878* (2013.01); *G16H 50/30* (2018.01); *A61B 2560/0252* (2013.01)

(58) Field of Classification Search
CPC ............... A61B 5/0537; A61B 5/4875; A61B 5/4878; A61B 2560/0252; G16H 50/30
See application file for complete search history.

(56) References Cited

U.S. PATENT DOCUMENTS

| 3,316,896 A | 5/1967 | Thomasset |
| 3,834,374 A | 9/1974 | Ensanian et al. |
| 3,851,641 A | 12/1974 | Toole et al. |
| 3,866,600 A | 2/1975 | Siepem |
| 3,871,359 A | 3/1975 | Pacela |
| 4,008,712 A | 2/1977 | Nyboer |
| 4,034,854 A | 7/1977 | Bevilacqua |

(Continued)

FOREIGN PATENT DOCUMENTS

| CA | 2231038 A1 | 11/1999 |
| CA | 2613524 A1 | 1/2007 |

(Continued)

OTHER PUBLICATIONS

English Translation of CN1180513A Published May 6, 1998.

(Continued)

*Primary Examiner* — Alex M Valvis
*Assistant Examiner* — Chanel J Jhin
(74) *Attorney, Agent, or Firm* — Knobbe, Martens, Olson & Bear, LLP

(57) ABSTRACT

A method of determining an indication of the hydration status relating to a subject. The method includes determining a measured impedance value for at least one body segment, and then; for each body segment, using the measured impedance values to determine at least one indicator at least partially indicative of a level of extracellular fluid. Indicators can then be used to determine an indication of the hydration status.

16 Claims, 16 Drawing Sheets

(56) References Cited

U.S. PATENT DOCUMENTS

| | | |
|---|---|---|
| 4,082,087 A | 4/1978 | Howson |
| 4,144,878 A | 3/1979 | Wheeler |
| RE30,101 E | 9/1979 | Kubicek et al. |
| 4,169,463 A | 10/1979 | Piquard |
| 4,184,486 A | 1/1980 | Papa |
| 4,291,708 A | 9/1981 | Frei et al. |
| 4,314,563 A | 2/1982 | Wheeler |
| 4,353,372 A | 10/1982 | Ayer |
| 4,365,634 A | 12/1982 | Bare et al. |
| 4,401,356 A | 8/1983 | Bare |
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,646,754 A | 3/1987 | Seale |
| 4,686,477 A | 8/1987 | Givens et al. |
| 4,688,580 A | 8/1987 | Ko et al. |
| 4,695,955 A | 9/1987 | Faisandier |
| 4,763,660 A | 8/1988 | Kroll et al. |
| 4,793,362 A | 12/1988 | Tedner |
| 4,832,608 A | 5/1989 | Kroll |
| 4,836,214 A | 6/1989 | Sramek |
| 4,890,630 A | 1/1990 | Kroll et al. |
| 4,895,163 A | 1/1990 | Libke et al. |
| 4,905,705 A | 3/1990 | Kizakevich et al. |
| 4,911,175 A | 3/1990 | Shizgal |
| 4,924,875 A | 5/1990 | Chamoun |
| 4,942,880 A | 7/1990 | Slovak |
| 4,951,682 A | 8/1990 | Petre |
| 5,020,541 A | 6/1991 | Marriott |
| 5,025,784 A | 6/1991 | Shao et al. |
| 5,063,937 A | 11/1991 | Ezenwa et al. |
| 5,078,134 A | 1/1992 | Heilman et al. |
| 5,086,781 A | 2/1992 | Bookspan |
| 5,101,828 A | 4/1992 | Welkowitz et al. |
| 5,143,079 A | 9/1992 | Frei et al. |
| 5,184,624 A | 2/1993 | Brown et al. |
| 5,197,479 A | 3/1993 | Hubelbank et al. |
| 5,199,432 A | 4/1993 | Quedens et al. |
| 5,208,429 A | 5/1993 | Field |
| 5,233,982 A | 8/1993 | Kohl |
| 5,246,008 A | 9/1993 | Mueller |
| 5,272,624 A | 12/1993 | Gisser et al. |
| 5,282,840 A | 2/1994 | Hudrlik |
| 5,284,142 A | 2/1994 | Goble et al. |
| 5,305,192 A | 4/1994 | Bonte et al. |
| 5,309,917 A | 5/1994 | Wang et al. |
| 5,311,878 A | 5/1994 | Brown et al. |
| 5,335,667 A | 8/1994 | Cha et al. |
| 5,351,697 A | 10/1994 | Cheney et al. |
| 5,353,802 A | 10/1994 | Ollmar |
| 5,372,141 A | 12/1994 | Gallup et al. |
| 5,381,333 A | 1/1995 | Isaacson et al. |
| 5,390,110 A | 2/1995 | Cheney et al. |
| 5,415,164 A | 5/1995 | Faupel et al. |
| 5,421,344 A | 6/1995 | Popp |
| 5,421,345 A | 6/1995 | Lekholm et al. |
| 5,423,326 A | 6/1995 | Wang et al. |
| 5,427,113 A | 6/1995 | Hiroshi |
| 5,449,000 A | 9/1995 | Libke et al. |
| 5,454,377 A | 10/1995 | Dzwonczyk et al. |
| 5,465,730 A | 11/1995 | Zadehkoochak et al. |
| 5,469,859 A | 11/1995 | Tsoglin et al. |
| 5,503,157 A | 4/1996 | Sramek et al. |
| 5,505,209 A | 4/1996 | Reining |
| 5,511,553 A | 4/1996 | Segalowitz |
| 5,526,808 A | 6/1996 | Kaminsky |
| 5,529,072 A | 6/1996 | Sramek |
| 5,544,662 A | 8/1996 | Saulnier et al. |
| 5,557,242 A | 9/1996 | Wetherell |
| 5,562,607 A | 10/1996 | Gyory |
| 5,575,929 A | 11/1996 | Yu et al. |
| 5,588,429 A | 12/1996 | Isaacson et al. |
| 5,596,283 A | 1/1997 | Mellitz et al. |
| 5,611,351 A | 3/1997 | Sato et al. |
| 5,615,689 A | 4/1997 | Kotler |
| 5,626,146 A | 5/1997 | Barber et al. |
| 5,679,022 A | 10/1997 | Cappa et al. |
| 5,704,355 A | 1/1998 | Bridges |
| 5,718,231 A | 2/1998 | Dewhurst et al. |
| 5,732,710 A | 3/1998 | Rabinovich et al. |
| 5,735,284 A | 4/1998 | Tsoglin et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,876,353 A | 3/1999 | Riff |
| 5,906,614 A | 5/1999 | Stern et al. |
| 5,919,142 A | 7/1999 | Boone et al. |
| 5,957,861 A | 9/1999 | Combs et al. |
| 5,964,703 A | 10/1999 | Goodman et al. |
| 5,974,910 A | 11/1999 | Paykin et al. |
| 6,006,125 A | 12/1999 | Kelly et al. |
| 6,011,992 A | 1/2000 | Hubbard et al. |
| 6,015,389 A | 1/2000 | Brown |
| 6,018,677 A | 1/2000 | Vidrine et al. |
| 6,026,323 A | 2/2000 | Skladnev et al. |
| 6,115,626 A | 9/2000 | Whayne et al. |
| 6,122,544 A | 9/2000 | Organ |
| 6,125,297 A | 9/2000 | Siconolfi |
| 6,129,666 A | 10/2000 | DeLuca et al. |
| 6,142,949 A | 11/2000 | Ubby |
| 6,151,520 A | 11/2000 | Combs |
| 6,151,523 A | 11/2000 | Rosell Ferrer et al. |
| 6,167,300 A | 12/2000 | Cherepenin et al. |
| 6,173,003 B1 | 1/2001 | Whikehart et al. |
| 6,208,890 B1 | 3/2001 | Sarrazin et al. |
| 6,228,033 B1 | 5/2001 | Koobi et al. |
| 6,233,473 B1 | 5/2001 | Shepherd et al. |
| 6,236,886 B1 | 5/2001 | Cherepenin et al. |
| 6,248,083 B1 | 6/2001 | Smith et al. |
| 6,253,100 B1 | 6/2001 | Zhdanov |
| 6,256,532 B1 | 7/2001 | Cha |
| 6,280,396 B1 | 8/2001 | Clark |
| 6,292,690 B1 | 9/2001 | Petrucelli et al. |
| 6,308,097 B1 | 10/2001 | Pearlman |
| 6,339,722 B1 | 1/2002 | Heethaar et al. |
| 6,354,996 B1 | 3/2002 | Drinan et al. |
| 6,376,023 B1 | 4/2002 | Mori |
| 6,432,045 B2 | 8/2002 | Lemperle et al. |
| 6,459,930 B1 | 10/2002 | Takehara et al. |
| 6,469,732 B1 | 10/2002 | Chang et al. |
| 6,472,888 B2 | 10/2002 | Oguma et al. |
| 6,496,725 B2 | 12/2002 | Kamada et al. |
| 6,497,659 B1 | 12/2002 | Rafert |
| 6,501,987 B1 | 12/2002 | Lovett et al. |
| 6,511,438 B2 | 1/2003 | Bernstein et al. |
| 6,512,949 B1 | 1/2003 | Combs et al. |
| 6,516,218 B1 | 2/2003 | Cheng et al. |
| 6,522,910 B1 | 2/2003 | Gregory |
| 6,532,384 B1 | 3/2003 | Fukuda et al. |
| 6,551,252 B2 | 4/2003 | Sackner et al. |
| 6,556,001 B1 | 4/2003 | Wiegand et al. |
| 6,560,480 B1 | 5/2003 | Nachaliel et al. |
| 6,561,986 B2 | 5/2003 | Baura et al. |
| 6,564,079 B1 | 5/2003 | Cory et al. |
| 6,569,160 B1 | 5/2003 | Goldin et al. |
| 6,584,348 B2 | 6/2003 | Glukhovsky |
| 6,602,201 B1 | 8/2003 | Hepp et al. |
| 6,615,077 B1 | 9/2003 | Zhu et al. |
| 6,618,616 B2 | 9/2003 | Iijima et al. |
| 6,623,312 B2 | 9/2003 | Merry et al. |
| 6,625,487 B2 | 9/2003 | Herleikson |

(56) References Cited

U.S. PATENT DOCUMENTS

| | | |
|---|---|---|
| 6,631,292 B1 | 10/2003 | Liedtke |
| 6,633,777 B2 | 10/2003 | Szopinski |
| 6,636,754 B1 | 10/2003 | Baura et al. |
| 6,643,543 B2 | 11/2003 | Takehara et al. |
| 6,658,296 B1 | 12/2003 | Wong et al. |
| 6,714,813 B2 | 3/2004 | Ishigooka et al. |
| 6,714,814 B2 | 3/2004 | Yameda et al. |
| 6,723,049 B2 | 4/2004 | Skladnev et al. |
| 6,724,200 B2 | 4/2004 | Fukuda |
| 6,725,089 B2 | 4/2004 | Komatsu et al. |
| 6,753,487 B2 | 6/2004 | Fujii et al. |
| 6,760,617 B2 | 7/2004 | Ward et al. |
| 6,763,263 B2 | 7/2004 | Gregory et al. |
| 6,768,921 B2 | 7/2004 | Organ et al. |
| 6,788,966 B2 | 9/2004 | Kenan et al. |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,840,907 B1 | 1/2005 | Brydon |
| 6,845,264 B1 | 1/2005 | Skladnev et al. |
| 6,870,109 B1 | 3/2005 | Villarreal |
| 6,906,533 B1 | 6/2005 | Yoshida |
| 6,922,586 B2 | 7/2005 | Davies |
| 6,936,012 B2 | 8/2005 | Wells |
| 6,940,286 B2 | 9/2005 | Wang et al. |
| 6,953,323 B2 | 10/2005 | Childers et al. |
| 6,976,973 B1 | 12/2005 | Ruddell et al. |
| 6,980,852 B2 | 12/2005 | Jersey-Willuhn et al. |
| 7,033,539 B2 | 4/2006 | Krensky et al. |
| 7,065,399 B2 | 6/2006 | Nakada |
| 7,072,710 B2 | 7/2006 | Chamney |
| 7,079,889 B2 | 7/2006 | Nakada |
| 7,096,061 B2 | 8/2006 | Arad |
| 7,122,012 B2 | 10/2006 | Bouton et al. |
| 7,130,680 B2 | 10/2006 | Kodama et al. |
| 7,148,701 B2 | 12/2006 | Park et al. |
| 7,149,573 B2 | 12/2006 | Wang |
| 7,164,522 B2 | 1/2007 | Kimura et al. |
| 7,169,107 B2 | 1/2007 | Jersey-Willuhn et al. |
| 7,175,606 B2 | 2/2007 | Bowman et al. |
| 7,184,820 B2 | 2/2007 | Jersey-Willluhn et al. |
| 7,184,821 B2 | 2/2007 | Belalcazar et al. |
| 7,186,220 B2 | 3/2007 | Stahmann et al. |
| 7,212,852 B2 | 5/2007 | Smith et al. |
| 7,214,107 B2 | 5/2007 | Powell et al. |
| 7,233,823 B2 | 6/2007 | Simond et al. |
| 7,251,524 B1 | 7/2007 | Hepp et al. |
| 7,270,580 B2 | 9/2007 | Bradley et al. |
| 7,288,943 B2 | 10/2007 | Matthiessen et al. |
| 7,313,435 B2 | 12/2007 | Nakada et al. |
| 7,317,161 B2 | 1/2008 | Fukuda |
| 7,336,992 B2 | 2/2008 | Shiokawa |
| 7,353,058 B2 | 4/2008 | Weng et al. |
| 7,354,417 B1 | 4/2008 | Levin et al. |
| 7,390,303 B2 | 6/2008 | Dafni |
| 7,440,796 B2 | 10/2008 | Woo et al. |
| 7,457,660 B2 | 11/2008 | Smith et al. |
| 7,477,937 B2 | 1/2009 | Iijima et al. |
| 7,496,450 B2 | 2/2009 | Ortiz Aleman et al. |
| 7,603,158 B2 | 10/2009 | Nachman |
| 7,603,171 B2 | 10/2009 | Eror et al. |
| 7,628,761 B2 | 12/2009 | Gozani et al. |
| 7,638,341 B2 | 12/2009 | Rubinsky et al. |
| 7,660,617 B2 | 2/2010 | Davis |
| 7,706,872 B2 | 4/2010 | Min et al. |
| 7,711,418 B2 | 5/2010 | Garber et al. |
| 7,729,756 B2 | 6/2010 | Mertelmeier et al. |
| 7,733,224 B2 | 6/2010 | Tran |
| 7,749,013 B2 | 7/2010 | Sato et al. |
| 7,907,977 B2 | 3/2011 | Stahmann et al. |
| 7,907,997 B2 | 3/2011 | Stahmann et al. |
| 7,917,202 B2 | 3/2011 | Chamney et al. |
| 7,983,853 B2 | 7/2011 | Wang et al. |
| 8,055,335 B2 | 11/2011 | Stylos |
| 8,068,906 B2 | 11/2011 | Chetham |
| 8,172,762 B2 | 5/2012 | Robertson |
| 8,285,356 B2 | 10/2012 | Bly et al. |
| 8,744,564 B2 | 6/2014 | Ward et al. |
| 9,724,012 B2 * | 8/2017 | Chetham ............... A61B 5/0537 |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0025139 A1 | 9/2001 | Pearlman |
| 2001/0049479 A1 | 12/2001 | Szopinski |
| 2001/0051774 A1 | 12/2001 | Littrup et al. |
| 2002/0022773 A1 | 2/2002 | Drinan |
| 2002/0022787 A1 | 2/2002 | Takehara et al. |
| 2002/0072682 A1 | 6/2002 | Hopman et al. |
| 2002/0072686 A1 | 6/2002 | Hoey et al. |
| 2002/0079910 A1 | 6/2002 | Fukuda |
| 2002/0093992 A1 | 7/2002 | Plangger |
| 2002/0106681 A1 | 8/2002 | Wexler |
| 2002/0109621 A1 | 8/2002 | Khair et al. |
| 2002/0123694 A1 | 9/2002 | Organ et al. |
| 2002/0138019 A1 | 9/2002 | Wexler et al. |
| 2002/0161311 A1 | 10/2002 | Ward et al. |
| 2002/0163408 A1 | 11/2002 | Fujii et al. |
| 2002/0194419 A1 | 12/2002 | Rajput et al. |
| 2003/0004403 A1 | 1/2003 | Drinan et al. |
| 2003/0004433 A1 | 1/2003 | Hirschman |
| 2003/0009111 A1 | 1/2003 | Cory |
| 2003/0023184 A1 | 1/2003 | Pitts-crick et al. |
| 2003/0028221 A1 | 2/2003 | Zhu et al. |
| 2003/0050570 A1 | 3/2003 | Kodama |
| 2003/0068914 A1 | 4/2003 | Merry et al. |
| 2003/0073916 A1 | 4/2003 | Yonce |
| 2003/0105410 A1 | 6/2003 | Pearlman |
| 2003/0105411 A1 | 6/2003 | Smallwood et al. |
| 2003/0120170 A1 * | 6/2003 | Zhu ..................... A61B 5/4869 |
| | | 600/547 |
| 2003/0120182 A1 | 6/2003 | Wilkinson et al. |
| 2003/0173976 A1 | 9/2003 | Wiegand et al. |
| 2003/0176808 A1 | 9/2003 | Masuo |
| 2003/0194894 A1 * | 10/2003 | Wariar ................ A61M 1/3653 |
| | | 439/191 |
| 2003/0216664 A1 | 11/2003 | Suarez |
| 2004/0015095 A1 | 1/2004 | Li et al. |
| 2004/0019292 A1 | 1/2004 | Drinan et al. |
| 2004/0054298 A1 | 3/2004 | Masuo et al. |
| 2004/0059242 A1 | 3/2004 | Masuo et al. |
| 2004/0073127 A1 | 4/2004 | Istvan et al. |
| 2004/0073130 A1 | 4/2004 | Bohm et al. |
| 2004/0077944 A1 | 4/2004 | Steinberg et al. |
| 2004/0116819 A1 | 6/2004 | Alt et al. |
| 2004/0158167 A1 | 8/2004 | Smith et al. |
| 2004/0167423 A1 | 8/2004 | Pillon et al. |
| 2004/0171963 A1 | 9/2004 | Takehara |
| 2004/0181163 A1 | 9/2004 | Wong et al. |
| 2004/0181164 A1 | 9/2004 | Smith et al. |
| 2004/0186392 A1 | 9/2004 | Ward et al. |
| 2004/0204658 A1 | 10/2004 | Dietz et al. |
| 2004/0210150 A1 | 10/2004 | Virtanen |
| 2004/0210158 A1 | 10/2004 | Organ et al. |
| 2004/0220632 A1 | 11/2004 | Burnes |
| 2004/0234113 A1 | 11/2004 | Miga |
| 2004/0236202 A1 | 11/2004 | Burton |
| 2004/0242989 A1 | 12/2004 | Zhu et al. |
| 2004/0243018 A1 | 12/2004 | Organ et al. |
| 2004/0252870 A1 | 12/2004 | Reeves et al. |
| 2004/0260167 A1 | 12/2004 | Leonhardt et al. |
| 2004/0267333 A1 | 12/2004 | Kronberg |
| 2004/0267344 A1 | 12/2004 | Stett et al. |
| 2005/0033281 A1 | 2/2005 | Bowman et al. |
| 2005/0039763 A1 * | 2/2005 | Kraemer ............... A61B 5/0537 |
| | | 600/300 |
| 2005/0070778 A1 | 3/2005 | Lackey et al. |
| 2005/0080460 A1 | 4/2005 | Wang et al. |
| 2005/0085743 A1 | 4/2005 | Hacker et al. |
| 2005/0098343 A1 | 5/2005 | Fukuda |
| 2005/0101875 A1 * | 5/2005 | Semler .................. A61B 5/282 |
| | | 600/509 |
| 2005/0107719 A1 | 5/2005 | Arad |
| 2005/0113704 A1 | 5/2005 | Lawson et al. |

(56) References Cited

U.S. PATENT DOCUMENTS

| | | |
|---|---|---|
| 2005/0117196 A1 | 6/2005 | Kimura et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177061 A1 | 8/2005 | Alanen et al. |
| 2005/0177062 A1* | 8/2005 | Skrabal ............... A61B 5/0535 600/547 |
| 2005/0192488 A1 | 9/2005 | Bryenton et al. |
| 2005/0192511 A1 | 9/2005 | Shiokawa |
| 2005/0201598 A1 | 9/2005 | Harel et al. |
| 2005/0203435 A1 | 9/2005 | Nakada |
| 2005/0215918 A1 | 9/2005 | Frantz et al. |
| 2005/0228309 A1 | 10/2005 | Fisher et al. |
| 2005/0251062 A1 | 11/2005 | Choi |
| 2005/0261743 A1 | 11/2005 | Kroll et al. |
| 2005/0283091 A1 | 12/2005 | Kink et al. |
| 2006/0004300 A1 | 1/2006 | Kennedy |
| 2006/0025701 A1 | 2/2006 | Kasahara |
| 2006/0041280 A1 | 2/2006 | Stahmann et al. |
| 2006/0052678 A1 | 3/2006 | Drinan |
| 2006/0064029 A1 | 3/2006 | Arad |
| 2006/0085048 A1 | 4/2006 | Cory et al. |
| 2006/0085049 A1 | 4/2006 | Cory et al. |
| 2006/0110962 A1 | 5/2006 | Powell et al. |
| 2006/0111652 A1 | 5/2006 | McLeod |
| 2006/0116599 A1 | 6/2006 | Davis |
| 2006/0122523 A1 | 6/2006 | Bonmassar et al. |
| 2006/0122540 A1* | 6/2006 | Zhu ............... A61B 5/0537 600/587 |
| 2006/0128193 A1 | 6/2006 | Bradley et al. |
| 2006/0135886 A1 | 6/2006 | Lippert et al. |
| 2006/0151815 A1 | 7/2006 | Graovac et al. |
| 2006/0184060 A1 | 8/2006 | Belacazar |
| 2006/0197509 A1 | 9/2006 | Kanamori et al. |
| 2006/0200033 A1 | 9/2006 | Keren et al. |
| 2006/0224079 A1 | 10/2006 | Washchuk |
| 2006/0224080 A1 | 10/2006 | Oku et al. |
| 2006/0241513 A1 | 10/2006 | Hatlestad et al. |
| 2006/0241719 A1 | 10/2006 | Foster et al. |
| 2006/0247543 A1 | 11/2006 | Cornish et al. |
| 2006/0247739 A1 | 11/2006 | Wahlstrand et al. |
| 2006/0258952 A1 | 11/2006 | Stahmann et al. |
| 2006/0264775 A1 | 11/2006 | Mills et al. |
| 2006/0264776 A1 | 11/2006 | Stahmann et al. |
| 2006/0270942 A1 | 11/2006 | McAdams |
| 2006/0293609 A1 | 12/2006 | Stahmann et al. |
| 2007/0007975 A1 | 1/2007 | Hawkins et al. |
| 2007/0010758 A1 | 1/2007 | Matthiessen et al. |
| 2007/0024310 A1 | 2/2007 | Tokuno et al. |
| 2007/0027402 A1 | 2/2007 | Levin et al. |
| 2007/0043303 A1 | 2/2007 | Osypka et al. |
| 2007/0049993 A1 | 3/2007 | Hofmann et al. |
| 2007/0087703 A1 | 4/2007 | Li et al. |
| 2007/0106342 A1 | 5/2007 | Schumann |
| 2007/0156061 A1 | 7/2007 | Hess |
| 2007/0188219 A1 | 8/2007 | Segarra |
| 2007/0246046 A1 | 10/2007 | Teschner et al. |
| 2007/0270707 A1 | 11/2007 | Belalcazar |
| 2007/0273504 A1 | 11/2007 | Tran |
| 2007/0276270 A1 | 11/2007 | Tran |
| 2008/0001608 A1 | 1/2008 | Saulnier et al. |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0027350 A1 | 1/2008 | Webler |
| 2008/0039700 A1 | 2/2008 | Drinan et al. |
| 2008/0051643 A1 | 2/2008 | Park et al. |
| 2008/0064981 A1 | 3/2008 | Gregory |
| 2008/0139957 A1 | 6/2008 | Hubbard et al. |
| 2008/0200802 A1 | 8/2008 | Bhavaraju et al. |
| 2008/0205717 A1 | 8/2008 | Reeves et al. |
| 2008/0247502 A1 | 10/2008 | Liao |
| 2008/0252304 A1 | 10/2008 | Woo et al. |
| 2008/0270051 A1 | 10/2008 | Essex et al. |
| 2008/0287823 A1 | 11/2008 | Chetham |
| 2008/0306400 A1 | 12/2008 | Takehara |
| 2008/0319336 A1* | 12/2008 | Ward ............... A61B 5/0537 600/547 |
| 2009/0018432 A1 | 1/2009 | He |
| 2009/0043222 A1 | 2/2009 | Chetham |
| 2009/0054952 A1 | 2/2009 | Glukhovsky et al. |
| 2009/0069708 A1 | 3/2009 | Hatlestad et al. |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0076410 A1 | 3/2009 | Libbus et al. |
| 2009/0082679 A1 | 3/2009 | Chetham |
| 2009/0084674 A1 | 4/2009 | Holzhacker et al. |
| 2009/0093730 A1 | 4/2009 | Grassl |
| 2009/0105555 A1 | 4/2009 | Dacso et al. |
| 2009/0143663 A1 | 6/2009 | Chetham |
| 2009/0177099 A1 | 7/2009 | Smith et al. |
| 2009/0209872 A1 | 8/2009 | Pop |
| 2009/0216140 A1 | 8/2009 | Skrabal |
| 2009/0216148 A1 | 8/2009 | Freed |
| 2009/0234244 A1 | 9/2009 | Tanaka |
| 2009/0240163 A1 | 9/2009 | Webler |
| 2009/0264727 A1 | 10/2009 | Markowitz |
| 2009/0264745 A1 | 10/2009 | Markowitz |
| 2009/0264776 A1 | 10/2009 | Vardy |
| 2009/0264791 A1 | 10/2009 | Gregory |
| 2009/0275854 A1 | 11/2009 | Zielinski |
| 2009/0275855 A1 | 11/2009 | Zielinski |
| 2009/0287102 A1 | 11/2009 | Ward |
| 2009/0318778 A1 | 12/2009 | Dacso et al. |
| 2009/0326408 A1 | 12/2009 | Moon |
| 2010/0007357 A1 | 1/2010 | Ammari et al. |
| 2010/0049077 A1 | 2/2010 | Sadleir |
| 2010/0056881 A1 | 3/2010 | Libbus et al. |
| 2010/0094160 A1 | 4/2010 | Eror et al. |
| 2010/0100003 A1 | 4/2010 | Chetham et al. |
| 2010/0106046 A1 | 4/2010 | Shochat |
| 2010/0109739 A1 | 5/2010 | Ironstone et al. |
| 2010/0145164 A1 | 6/2010 | Howell |
| 2010/0152605 A1 | 6/2010 | Ward |
| 2010/0168530 A1 | 7/2010 | Chetham et al. |
| 2010/0191141 A1 | 7/2010 | Aberg |
| 2010/0228143 A1 | 9/2010 | Teschner et al. |
| 2010/0234701 A1 | 9/2010 | Cho et al. |
| 2011/0034806 A1 | 2/2011 | Hartov et al. |
| 2011/0046505 A1 | 2/2011 | Cornish et al. |
| 2011/0054344 A1 | 3/2011 | Slizynski |
| 2011/0060239 A1 | 3/2011 | Gaw |
| 2011/0060241 A1 | 3/2011 | Martinsen et al. |
| 2011/0082383 A1 | 4/2011 | Cory et al. |
| 2011/0118619 A1 | 5/2011 | Burton et al. |
| 2011/0208084 A1 | 8/2011 | Seoane Martinez |
| 2011/0230784 A2 | 9/2011 | Slizynski |
| 2011/0245712 A1 | 10/2011 | Patterson |
| 2011/0274327 A1 | 11/2011 | Wehnes et al. |
| 2011/0282180 A1 | 11/2011 | Goldkuhl et al. |
| 2012/0071772 A1 | 3/2012 | Chetham |
| 2012/0095352 A1 | 4/2012 | Tran |
| 2012/0165884 A1 | 6/2012 | Xi |
| 2012/0238896 A1 | 9/2012 | Garber et al. |
| 2013/0102873 A1 | 4/2013 | Hamaguchi |
| 2013/0165760 A1 | 6/2013 | Erlinger et al. |
| 2013/0165761 A1 | 6/2013 | De Limon et al. |
| 2014/0148721 A1 | 5/2014 | Erlinger |
| 2014/0371566 A1 | 12/2014 | Raymond et al. |

FOREIGN PATENT DOCUMENTS

| | | |
|---|---|---|
| CA | 2615845 A1 | 1/2007 |
| CA | 2638958 | 11/2011 |
| CN | 1180513 A | 5/1998 |
| CN | 1236597 A | 12/1999 |
| CN | 1329875 A | 1/2002 |
| CN | 1366694 A | 8/2002 |
| CN | 101385203 A | 3/2009 |
| DE | 2912349 A1 | 10/1980 |
| EP | 249823 A1 | 12/1987 |
| EP | 0339471 A2 | 11/1989 |
| EP | 349043 A2 | 1/1990 |

(56) References Cited

FOREIGN PATENT DOCUMENTS

| | | |
|---|---|---|
| EP | 357309 A2 | 3/1990 |
| EP | 377877 A1 | 7/1990 |
| EP | 0581073 A2 | 2/1994 |
| EP | 662311 A1 | 7/1995 |
| EP | 0339471 B1 | 3/1997 |
| EP | 0865763 A2 | 9/1998 |
| EP | 869360 A2 | 10/1998 |
| EP | 1078597 A2 | 2/2001 |
| EP | 1080686 A1 | 3/2001 |
| EP | 1112715 A1 | 7/2001 |
| EP | 1114610 A1 | 7/2001 |
| EP | 1118308 A1 | 7/2001 |
| EP | 1146344 A1 | 10/2001 |
| EP | 1177760 A1 | 2/2002 |
| EP | 1219937 A1 | 7/2002 |
| EP | 1238630 A2 | 9/2002 |
| EP | 1247487 A1 | 10/2002 |
| EP | 1283539 A1 | 2/2003 |
| EP | 1329190 A1 | 7/2003 |
| EP | 1080686 B1 | 3/2004 |
| EP | 1452131 A1 | 9/2004 |
| EP | 1553871 A1 | 7/2005 |
| EP | 1629772 A1 | 3/2006 |
| EP | 1903938 A1 | 4/2008 |
| EP | 1909642 A1 | 4/2008 |
| EP | 1948017 A1 | 7/2008 |
| EP | 1353595 B1 | 8/2008 |
| FR | 2486386 A1 | 1/1982 |
| FR | 2748928 A1 | 11/1997 |
| GB | 213558 A | 6/1984 |
| GB | 2260416 A | 4/1993 |
| GB | 2426824 A | 12/2006 |
| JP | 04-096733 A | 3/1992 |
| JP | 06-000168 A | 1/1994 |
| JP | 08-191808 A | 7/1996 |
| JP | 09-051884 A | 2/1997 |
| JP | 09-220209 A | 8/1997 |
| JP | 10-000185 A | 1/1998 |
| JP | 10-014898 A | 1/1998 |
| JP | 10-014899 A | 1/1998 |
| JP | 10-080406 A | 3/1998 |
| JP | 10-225521 A | 8/1998 |
| JP | 11-070090 A | 3/1999 |
| JP | 2000-107138 A | 4/2000 |
| JP | 2000-139867 A | 5/2000 |
| JP | 2001-037735 A | 2/2001 |
| JP | 2001-061804 A | 3/2001 |
| JP | 2001-070273 A | 3/2001 |
| JP | 2001-224568 A | 8/2001 |
| JP | 2001-321352 A | 11/2001 |
| JP | 2002-330938 A | 11/2002 |
| JP | 2003-2116805 A | 4/2003 |
| JP | 2003-230547 A | 8/2003 |
| JP | 2004-61251 A | 2/2004 |
| JP | 2005-099186 A | 4/2005 |
| JP | 2008-022995 A | 2/2008 |
| NL | 001019789 C2 | 7/2003 |
| RU | 2112416 C1 | 6/1998 |
| RU | 2138193 C1 | 9/1999 |
| SU | 1132911 A1 | 1/1985 |
| WO | WO 1988/007392 A1 | 10/1988 |
| WO | WO 1991/19454 A1 | 12/1991 |
| WO | WO 1993/18821 A1 | 9/1993 |
| WO | WO 1994/10922 A1 | 5/1994 |
| WO | WO 1996-01586 A1 | 1/1996 |
| WO | WO 1996/012439 A1 | 5/1996 |
| WO | WO 1996/032652 A1 | 10/1996 |
| WO | WO 1997-011638 A2 | 4/1997 |
| WO | WO 1997/014358 A1 | 4/1997 |
| WO | WO 1997/24156 A1 | 7/1997 |
| WO | WO 1997/43000 A1 | 11/1997 |
| WO | WO 1998/06328 A1 | 2/1998 |
| WO | WO 1998/023204 A1 | 6/1998 |
| WO | WO 1998/33553 A1 | 8/1998 |
| WO | WO 1998/051211 A1 | 11/1998 |
| WO | WO 1998/54792 A1 | 12/1998 |
| WO | WO 1999/42034 A2 | 8/1999 |
| WO | WO 1999/48422 A1 | 9/1999 |
| WO | WO 2000/019886 A1 | 4/2000 |
| WO | WO 2000/40955 A1 | 7/2000 |
| WO | WO 2000/78213 A2 | 12/2000 |
| WO | WO 2000/79255 A1 | 12/2000 |
| WO | WO 2001/027605 A1 | 4/2001 |
| WO | WO 2001/050954 A1 | 7/2001 |
| WO | WO 2001/52733 A1 | 7/2001 |
| WO | WO 2001/067098 A1 | 9/2001 |
| WO | WO 2001/78831 A2 | 10/2001 |
| WO | WO 2001/082323 A1 | 11/2001 |
| WO | WO 2002/047548 A1 | 6/2002 |
| WO | WO 2002/053028 A2 | 7/2002 |
| WO | WO 2002/062214 A1 | 8/2002 |
| WO | WO 2002/094096 A1 | 11/2002 |
| WO | WO 2002/100267 A1 | 12/2002 |
| WO | WO 2004/000115 A1 | 12/2003 |
| WO | WO 2004/021880 A1 | 3/2004 |
| WO | WO 2004/026136 A1 | 4/2004 |
| WO | WO 2004/030535 A1 | 4/2004 |
| WO | WO 2004/032738 A1 | 4/2004 |
| WO | WO 2004/043252 A1 | 5/2004 |
| WO | WO 2004/047635 A1 | 6/2004 |
| WO | WO 2004/047636 A1 | 6/2004 |
| WO | WO 2004/047638 A1 | 6/2004 |
| WO | WO 2004/048983 A | 6/2004 |
| WO | WO 2004/049936 A2 | 6/2004 |
| WO | WO 2004/083804 A2 | 9/2004 |
| WO | WO 2004/084087 A1 | 9/2004 |
| WO | WO 2004/084723 A1 | 10/2004 |
| WO | WO 2004/084724 A1 | 10/2004 |
| WO | WO 2004/098389 A2 | 11/2004 |
| WO | WO 2005/010640 A2 | 2/2005 |
| WO | WO 2005/018432 A2 | 3/2005 |
| WO | WO 2005/027717 A2 | 3/2005 |
| WO | WO 2005/051163 A2 | 6/2005 |
| WO | WO 2005/051194 A1 | 6/2005 |
| WO | WO 2005/084539 A1 | 9/2005 |
| WO | WO 2005/122881 A1 | 12/2005 |
| WO | WO 2005/122888 A1 | 12/2005 |
| WO | WO 2006/045051 A | 4/2006 |
| WO | WO 2006/056074 A1 | 6/2006 |
| WO | WO 2006/129108 A1 | 12/2006 |
| WO | WO 2006/129116 A1 | 12/2006 |
| WO | WO 2007/002991 A1 | 1/2007 |
| WO | WO 2007/002992 A1 | 1/2007 |
| WO | WO 2007/002993 A1 | 1/2007 |
| WO | WO 2007/009183 A1 | 1/2007 |
| WO | WO 2007/014417 A1 | 2/2007 |
| WO | WO 2007/041783 A1 | 4/2007 |
| WO | WO 2007/056493 A1 | 5/2007 |
| WO | WO 2007/070997 A1 | 6/2007 |
| WO | WO 2007/089278 A1 | 8/2007 |
| WO | WO 2007/128952 A1 | 11/2007 |
| WO | WO 2008/011716 A1 | 1/2008 |
| WO | WO 2008/064426 A1 | 6/2008 |
| WO | WO 2008/119166 A1 | 10/2008 |
| WO | WO 2008/138062 A1 | 11/2008 |
| WO | WO 2009/027812 A2 | 3/2009 |
| WO | WO 2009/036369 A1 | 3/2009 |
| WO | WO 2009/059351 A1 | 5/2009 |
| WO | WO 2009/068961 A2 | 6/2009 |
| WO | WO 2009/100491 A1 | 8/2009 |
| WO | WO 2009/112965 A1 | 9/2009 |
| WO | WO 2010/003162 A1 | 1/2010 |
| WO | WO 2010/029465 A2 | 3/2010 |
| WO | WO 2010/051600 A1 | 5/2010 |
| WO | WO 2010/060152 A | 6/2010 |
| WO | WO 2010/069023 A2 | 6/2010 |
| WO | WO 2010/076719 A1 | 7/2010 |
| WO | WO 2011/018744 A1 | 2/2011 |
| WO | WO 2011/022868 A1 | 2/2011 |
| WO | WO 2011/050393 A1 | 5/2011 |
| WO | WO 2011/075769 A1 | 6/2011 |
| WO | WO 2011/113169 A1 | 9/2011 |

(56) References Cited

FOREIGN PATENT DOCUMENTS

| WO | WO 2011/136867 A1 | 11/2011 |
|---|---|---|
| WO | WO 2014/176420 A1 | 10/2014 |

OTHER PUBLICATIONS

English Translation of CN12336597 Published Dec. 1, 1999.
English Translation of CN1329875A Published Jan. 9, 2002.
English Translation of JP2001037735 Published Feb. 13, 2001.
English Translation of JP20011061804 Published Mar. 13, 2001.
English Translation of JP2002502274 Published Jan. 22, 2002.
English Translation of JP2003502092 Published Jan. 21, 2003.
English Translation of JP2006501892 Published Jan. 19, 2006.
English Translation of JP2008502382 Published Jan. 31, 2008.
English Translation of JP2010526604 Published Aug. 5, 2010.
English Translation of WO9948422 Published Sep. 20, 1999.
English Translation of WO0152733 Published Jul. 26, 2001.
Abdullah M. Z.; Simulation of an inverse problem in electrical impedance tomography using resistance electrical network analogues; International Journal of Electrical Engineering Education; Oct. 1999; 36 (4): 311-324.
Al-Hatib, F.; Patient Instrument Connection Errors in Bioelectrical Impedance Measurement; Physiological Measurement; May 2, 1998; 19(2): 285-296.
Bella et al., "Relations of left ventrical mass to fat-free and adipose body mass: the strong heart study," Circulation, vol. 98, pp. 2538-2544, Dec. 8, 1998.
Bernstein; "A new stroke volume equation for thoracic electrical bio impedance," Critical Care Medicine; 198~;vol. 14; pp. 904-909.
Blad and Baldetorp, "Impedance spectra of tumour tissue in comparison with normal tissue; a possible clinical application for electrical impedance tomography," Physiol. Meas., 1996, pp. A105-A115, vol. 17.
Boulier et al.; Fat-Free Mass Estimation by Two Electrode Impedance Method; American Journal of Clinical Nutrition; 1990; 52: 581-585.
Bracco et al.; Bedside determination of fluid accumulation after cardiac surgery usign segmental bioelectrical impedance; Critical Care Medicine, 1998; 26(6): 1065-1070.
Brown et al.; Relation between tissue structure and imposed electrical current flow in cervical neoplasia; The Lancet; Mar. 11, 2000; 355 (9207): 892-895.
Chaudary et al.; Dielectric Properties of Normal & Malignant Human Breast Tissues at Radiowave and Microwave Frequencies; Indian Journal of Biochemistry & Biophysics; 1984; 21(1): 76-79.
Chetham, Matthew; U.S. Appl. No. 11/629,804 entitled "Cardiac monitoring system," filed Dec. 15, 2006.
Chetham, Matthew; U.S. Appl. No. 11/776,456 entitled "Cardiac monitoring system," filed Jul. 11, 2007.
Chetham, Matthew; U.S. Appl. No. 11/993,842 entitled "Pulmonary monitoring system," filed Dec. 21, 2007.
Chetham, Matthew; U.S. Appl. No. 11/996,065 entitled "Index determination," filed Jan. 19, 2008.
Chiolero et al.; Assessment of changes in body water by bioimpedance in acutely ill surgical patients; Intensive Care Medicine, 1992; 18: 322-326.
Cumlea et al.; Bioelectrical impedance and body composition: present status and future directions; Nutrition Reviews, 1994; 52(4): 123-131.
Cornish et al.; Alteration of the extracellular and total body water volumes measured by multiple frequency bioelectrical impedance analysis; Nutrition Research; 1994; 14(5): 717-727.
Cornish et al.; Bioelectrical impedance for monitoring the efficacy of lymphoedema treatment programmes; Breast Cancer Research and Treatment, 1996; 38: 169-176.
Cornish et al.; Data analysis in multiple-frequency bioelectrical impedance analysis; Physiological Measurement, Institute of Physics Publishing, Bristol, GB, 1998; 19(2): 275-283.
Cornish et al.; Early diagnosis of lymphoedema in post-surgery breast cancer patients; Annals New York Academy of Sciences; May 2000; 571-575.
Cornish et al.; Early diagnosis of lymphedema using multiple frequency bioimpedance; Lymphology; Mar. 2001; 34: 2-11.
Cornish et al.; Quantification of lymphoedema using multi-frequency bioimpedance; Applied Radiation and Isotopes, Elsevier, Oxford, GB, 1998; 49(5/6): 651-652.
d'Entremont et al. "Impedance spectroscopy: an accurate method of differentiating between viable and ischaemic or infracted muscle tissue," Medical & Biological Engineering & Computing 2002, vol. 40.
De Lorenzo et al.; Predicting body cell mass with bioimpedance by using theoretical methods: a technological review; J_ Appl. Physiol., 1997; 82(5): 1542-58.
De Luca et al.; Use of low-frequency electrical impedance measurements to determine phospholipid content in amniotic fluid; Physics in Medicine and Biology, 1996; 41: 1863-1869.
Derwent; Abstract No. 97-474414, JP 09 220209 A (Sekisui Chem, Ind. Co. Ltd.), Aug. 26, 1997; Abstract.
Derwent; Abstract No. 98-138541, JP 10 014898 A (Sekisui Chem, Ind. Co. Ltd.), Jan. 20, 1998; Abstract.
Derwent; Abstract No. 99-247542, JP 11 070090 A (Sekisui Chem. Ind. Co. Ltd.), Mar. 16, 1999; Abstract.
Derwent; Abstract No. 98-138542, JP 10 014899 A (Sekisui Chem, Ind. Co. Ltd.), Feb. 20, 1998; Abstract.
Deurenberg et al.; Multi-frequency bioelectrical impedance: a comparison between the Cole-Cole modelling and Hanai equations with the classical impedance index approach; Annals of Human Biology, 1996; 23(1): 31-41.
Dines et al.; Analysis of electrical conductivity imaging; Geophysics; Jul. 1981; 46 (7): 1025-1036.
Edwards, "A Modified Pseudosection for Resistivity and IP," Geophysics, Aug. 1977, pp. 1020-1036, vol. 42. No. 5.
Ellis, K.J. et al., "Human hydrometry: comparison of multifrequency bioelectrical impedance with 2H20 and bromine dilution," Journal of Applied Physiology, vol. 85, No. 3, pp. 1056-1062, 1998.
European Search Report for EP 07718972.8-1265 / 2020918 (Impedimed, Ltd.), dated Mar. 2, 2010, 4 pages.
Fansan Zhu et al. "Dynamics of segmental extracellular volumes during changes in body position by bioimpedance analysis Journal of American Physiological society 1998".
Forslund et al., Evaluation of modified multicompartment models to calculate body composition in healthy males, Am. J_ of Clin. Nutrition, 1996; 63: 856-62.
Gersing, E.; Impedance Spectroscopy on Living Tissue for Determination of the State of Organs; Bioelectrochemistry and Bioenergetics; 1998; 45: 145-149.
Gerth et al., A computer-based bioelectrical impedance spectroscopic system for noninvasive assessment of compartmental fluid redistribution, 1990; 446-453.
Gudivaka et al.; Single- and multifrequency models for bioelectrical impedance analysis of body water compartments; J_ Appl. Physiol., 1999; 87(3): 1087-96.
Hansen, "On the influence of shape and variations in conductivity of the sample on four-point measurements," Appl. Sci. Res., 1959, pp. 93-104, section B, vol. 8.
Iacobellis et al., "Influence of excess fat on cardiac morphology and function: study in uncomplicated obesity," Obesity Research, vol. 10, No. 8, pp. 767-773, Aug. 8, 2002.
Igei, "On the Small-Scale Variability of Electrical Soil Properties and its influence on Geophysical Measurements," Dissertation, University of Frankfurt, 2007, pp. 1-188.
Jones, C.H. et al., "Extracellular fluid volume determined by bioelectric impedance and serum albumin in CAPO Patients," Nephrology Dialysis Transplantation, vol. 13, pp. 393-397, 1998.
Jossinet et al.; A study for breast imaging with a circular array of impedance electrodes; Proc. Vth Int. Conf. Bioelectrical Impedance, 1981, Tokyo, Japan; 1981; 83-86.
Jossinet et al.; Technical Implementation and Evaluation of a Bioelectrical Breast Scanner; Proc. 10$^{th}$ Int. Conf. IEEE Engng. Med. Biol., 1988, New Orleans, USA (Imped. Imaging II); 1988; 1: 289.

(56) References Cited

OTHER PUBLICATIONS

Kanai et al.; Electrical measurement offluid distribution in legs and arms; Medical Progress through Technology, 1987; 12: 159-170.

Kim et al.; Bioelectrical impedance changes in regional extracellular fluid alterations; Electromyography and Clinical Neurophysiology, 1997; 37: 297-304.

Kyle et al., "Bioelectrical impedance analysis—Part I: review of principals and methods," Clinical Nutrition, 2004, pp. 1226-1243, vol. 23.

Loke and Barker, "Least-squares deconvolution of apparent resistivity pseudosections," Geophysics, Nov.-Dec. 1995, pp. 1682-1690, vol. 60, No. 6.

Lorenzo et al., "Determination of Intracellar Water by Multifrequency Bioelectrical Impedance," Ann. Nutr. Metab., 1995, pp. 177-184, vol. 39.

Man et al.; Results of Preclinical Tests for Breast Cancer Detection by Dielectric Measurements; XII Int. Conf. Med. Biol. Engng. 1979, Jerusalem, Israel. Springer Int., Berlin; 1980; Section 30.4.

Mallar, J.A.; Application of Total Body Impedance to the Critically Ill Patient; New Horizons; 1996; 4(4): 493-503.

McAdams and Jossinet, "Tissue impedance: a historical overview," Physiol. Meas., 1995, pp. A1-A13, vol. 16.

McEwan and Holder, "Battery powered and wireless Electrical Impedance Tomography Spectroscopy Imaging using Bluetooth," IFMBE Proceedings, 2007, pp. 798-801, vol. 16.

Karason et al., "Impact of blood pressure and insulin on the relationship between body fat and left ventricular structure," European Heart Journal, vol. 24, pp. 1500-1505, 2003.

Kinouchi et al. "Fast in vivo measurements of local tissue impedance using needle electrodes" Medical and Biological Engineering and Computing Sep. 1997.

Liu et al.; Primary multi-frequency data analyze in electrical impedance scanning; Proceedings of the IEEE-EMBS 2005, 27th Annual Int'l Conference of the Engineering in Med. and Biology Soc., Shanghai, China, Sep. 4, 2005; 1504-1507.

Lozano et al.; Two-frequency impedance plethysmograph: real and imaginary parts; Medical & Biological Engineering & Computing; Jan. 1990; 28(1): 38-42.

Lukaski et al.; Estimation of Body Fluid Volumes using Tetrapolar Bioelectrical Impedance Measurements; Aviation, Space, and Environmental Medicine; Dec. 1988; 1163-1169.

McAdams et al.; Tissue impedance: a historical overview; Physiological Measurement, Institute of Physics Publishing, Bristol, GB; 16 (3A); pp. A1-A13; Aug. 1, 1995.

McCullagh, W. A., et al., Bioelectrical impedance analysis measures the ejection fraction of the calf muscle pump, IFMBE Proceedings, 2007; vol. 17, p. 619.

McDougal et al.; Body Composition Measurements from Whole Body Resistance and Reactance; Surgical Forum; 1986; 36: 43-44.

Osterman et al.; Multifrequency electrical impedance imaging: preliminary in vivo experience in breast; Physiological Measurement; Feb. 2000; 21 (1): 99-109.

Ott et al.; Bioelectrical Impedance Analysis as a Predictor of Survival in Patients with Human Immunodeficiency Virus Infection; Journal of Acquired Immune Deficiency Syndromes and Human Retrovirology; 1995; 9: 20-25.

Pethig et al.; The Passive Electrical Properties of Biological Systems: Their Significance in Physiology, Biophysics and Biotechnology; Physics in Medicine and Biology; 1987; 32: 933-970.

Piperno et al.; Breast Cancer Screening by Impedance Measurements; Frontiers of Medical & Biological Engineering; 1990; 2: 111-117.

Rigaud et al.; Bioelectrical impedance techniques in medicine; Critical Reviews in Biomedical Engineering, 1996; 24 (4-6): 257-351.

Roy and Apparao, "Depth of investigation in direct current methods," Geophysics, Oct. 1971, pp. 943-959, vol. 36, No. 5.

Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; Oct. 31, 1996; 5: 1934-1935.

Skidmore et al.; A Data Collection System for Gathering Electrical Impedance Measurements from the Human Breast; Clinical Physics Physiological Measurement; 1987; 8: 99-102.

Sollish et al.; Microprocessor-assisted Screening Techniques; Israel Journal of Medical Sciences; 1981; 17: 859-8.

Steiiaert et al.; The use of multi-frequency impedance to determine total body water and extracellular water in obese and lean female individuals; International Journal of Obesity, 1997; 21: 930-934.

Surowiec et al.; Dielectric Properties of Breast Carcinoma and the Surrounding Tissues; IEEE Transactions on Biomedical Engineering; 1988; 35: 257-263.

Tedner, B.; Equipment using Impedance Technique for Automatic Recording of Fluid-Volume Changes during Hemodialysis; Medical & Biological Engineering & Computing; 1983; 285-290.

Thomas et al.; Bioelectrical impedance analysis for measurement of body fluid volumes—A review; Journal of Clinical Engineering; 1992; 17(16): 505-510.

Thomas, et al.; "Bioimpedance spectrometer in the determination of body water compartments: Accuracy and clinical significance;" Appl. Radiation. Isotopes; vol. 49, No. 5/6; pp. 447-455; 1998.

Thomas, B.J., "Future Technologies," Asia Pacific Journal Clinical Nutrition, vol. 4, pp. 157-159, 1995.

Van Loan et al.; Use of bioelectrical impedance spectroscopy (BIS) to measure fluid changes during pregnancy; J_ Appl. Physiol., 1995; 78:137-42.

Ulgen et al.; Electrical Parameters of Human Blood; Database accession No. 6408967 & Proceedings of the 20th Annual International Conference of the IEEE Engineering in Medicine and Biology Soc., 1998; 20(6): 2983-2986, IEEE Piscataway, NJ.

Ward et al.; Determination of Cole parameters in multiple frequency bioelectrical impedance analysis using only the measurement of impedances; Four-frequency fitting; Physiological Measurement; Sep. 2006; 27 (9): 839-850.

Ward et al.; "Multi-frequency bioelectrical impedance augments the diagnosis and management of lymphoedema in post-mastectomy patients"; European J_ of Clin. Investigation, 1992; 22: 751-754.

Ward et al.; There is a better way to measure Lymphedema; National Lymphedema Network Newsletter; Oct. 1995;7 (4): 89-92.

Wilson et al., "Feasibility studies of electrical impedance spectroscopy of monitoring tissue response to photodynamic therapy," SPIE, May 1998, pp. 69-80, vol. 3247.

Woodrow, G. et al., "Effects of icodextrin in automated peritoneal dialysis on blood pressure and bioelectrical impedance analysis," Nephrology Dialysis Transplantation, vol. 15, pp. 862-866, 2000.

Yoshinaga et al., "Effect of total adipose weight and systemic hypertension on left ventricle mass in children," American Journal of Cardiology, vol. 76, pp. 785-787, Oct. 15, 1995.

Zhu et al.; Segment-specific resistivity improves body fluid volume estimates from bioimpedance spectroscopy in hemodialysis patients; J_ Appl. Physiol., 2005; 100: 717-724.

\* cited by examiner

HYDRATION STATUS MONITORING

BACKGROUND OF THE INVENTION

The present invention relates to a method and apparatus for determining one or more indicators of a subject's hydration status and in particular to a method and apparatus for monitoring a subject's hydration status during a dialysis procedure.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

One existing technique for determining biological parameters relating to a subject, involves the use of bioelectrical impedance. This involves measuring the electrical impedance of a subject's body using a series of electrodes placed on the skin surface. Changes in electrical impedance at the body's surface are used to determine parameters, such as changes in fluid levels, associated with the cardiac cycle or oedema.

Maintaining hemostasis during hemodialysis is recommended to minimise cardiovascular and other associated risks. Oedema is difficult to detect until the interstitial fluid volume has risen to approximately 30% above normal, whilst severe dehydration can develop before the onset of clinical symptoms. The current method of evaluating hydration status of dialysis patients based on blood pressure and body weight changes over time can be misleading since these parameters are complex variables related to other physiologic mechanisms.

SUMMARY OF THE PRESENT INVENTION

In a first broad form the present invention provides a method of determining an indication of the hydration status relating to a subject, the method including, in a processing system:
a) determining a measured impedance value for at least one body segment;
b) for each body segment, and using the measured impedance values, determining at least one indicator, the indicator being at least partially indicative of a level of extracellular fluid;
c) determining an indication of the hydration status using at least one determined indicator.

Typically the method includes, in the processing system:
a) comparing the at least one indicator to at least one of:
 i) a predetermined reference;
 ii) an indicator determined for at least one other body segment; and,
 iii) a previously determined indicator; and,
b) determining an indication of the hydration status using the results of the comparison.

Typically the reference includes at least one of:
a) a predetermined threshold;
b) a tolerance determined from a normal population;
c) a predetermined range; and,
d) an indicator previously determined for the subject.

Typically the indicator is at least one of:
a) an index (I) of the ratio of extra- to intra-cellular fluid; and,
b) an extracellular fluid volume.

Typically the method includes, in the processing system:
a) determining a plurality of measured impedance values for each body segment, each measured impedance value being measured at a corresponding measurement frequency; and,
b) determining impedance parameter values based on the plurality of measured impedance values, the indicator being at least partially based on the determined impedance parameter values.

Typically the parameter values include $R_0$ and $R_\infty$, wherein:
$R_0$ is the resistance at zero frequency; and,
$R_\infty$ is the resistance at infinite frequency.

Typically the method includes:
a) monitoring changes over time for at least one of:
 i) $R_0$;
 ii) $R_\infty$;
 iii) a difference between $R_0$ and $R_\infty$;
b) a vector indication of an impedance measurement.

Typically the method includes, in the processing system:
a) determining values for parameters $R_0$ and $R_\infty$ from the measured impedance values; and,
b) determining the indicator by calculating the index (I) using the equation:

$$I = \frac{R_\infty}{R_0 - R_\infty}$$

Typically the method includes, in the processing system, determining the parameter values using the equation:

$$Z = R_\infty + \frac{R_0 - R_\infty}{1 + (j\omega\tau)^{(1-\alpha)}}$$

where:
Z is the measured impedance at angular frequency $\omega$,
$\tau$ is a time constant, and
$\alpha$ has a value between 0 and 1.

Typically the method includes, in the processing system:
a) determining the impedance of each body segment at four discrete frequencies; and,
b) determining values for the parameters by solving the equation using four simultaneous equations.

Typically the method includes, in the processing system, determining the parameter values by:
a) determining a complex impedance locus using the measured impedance values; and,
b) using the complex impedance locus to determine the parameter values.

Typically the indicator for a body segment is the extracellular fluid volume determined using the equation:

$$ECV_{Segment} = C_{Segment} \rho_{Segment} \left( \frac{L^2_{Segment}}{R_{Segment}} \right)$$

Where ECV=Extracellular fluid volume
$C_{Segment}$=Geometry Constant which is 1 for an arm or leg and 4 for the thoracic cavity
$L_{Segment}$=Length of the segment in cm $R_{Segment}$=Resistance of the segment in Ohm
$\rho_{Segment}$=Resistivity coefficient which is nominally 47 Ohm/cm Typically the method includes determining an indicator for the entire body the equation:

$$ECV_{Total}=2(ECV_{arm}+ECV_{leg})+ECV_{trunk}$$

Typically the second body segment and the at least one other body segment are different types of body segment.

Typically the body segments are limbs.

Typically the body segment includes at least one of:
a) a calf; and,
b) a bicep.

Typically the method includes, in the computer system:
a) determining a correction factor; and
b) determining the hydration status using the correction factor.

Typically the correction factor is indicative of at least one of:
a) a subject orientation or posture;
b) a subject skin temperature; and,
c) a subject ethnicity.

Typically the method includes, in the computer system:
a) determining a subject orientation; and
b) determining the hydration status using the orientation.

Typically the method includes, in the computer system:
a) determining a first indicator at a first subject orientation;
b) determining a second indicator at a second subject orientation; and
c) determining the hydration status using the difference between the first and second indicators.

Typically the method includes, in the computer system:
a) determining a first indicator at a first time;
b) determining a second indicator at a second time; and
c) determining the hydration status using the difference between the first and second indicators.

Typically the method includes, in the computer system, displaying an indication of at least one of:
a) parameter values;
b) the indicator;
c) an extracellular fluid volume; and,
d) a ratio of extra-cellular to intra-cellular fluid.

Typically the method includes, in the processing system:
a) receiving data representing at least one measured impedance value; and,
b) generating a representation of the at least one measured impedance value.

Typically the method includes, in the processing system:
a) selecting a representation type based on a selected impedance measurement type; and,
b) generating the representation in accordance with the selected representation type.

Typically the representation is in the form of at least one of:
a) a Complex impedance plot;
b) an argand diagram;
c) a list of impedance values;
d) a reactance against frequency plot; and,
e) resistance against frequency plot.

Typically the method includes, in the processing system:
a) receiving data representing at least one measured impedance value;
b) processing the at least one measured impedance value to determine at least one impedance parameter; and,
c) generating a representation of the at least one impedance parameter.

Typically the method includes, in the processing system:
a) causing one or more electrical signals to be applied to the subject using a first set of electrodes, the one or more electrical signals having a plurality of frequencies;
b) determining an indication of electrical signals measured across a second set of electrodes applied to the subject in response to the applied one or more signals;
c) determining from the indication and the one or more applied signals, an instantaneous impedance value at each of the plurality of frequencies; and,
d) determining the indicator using the instantaneous impedance values.

Typically the electrodes are positioned in accordance with the theory of equal potentials.

Typically the positioning of the electrodes includes:
a) a first current supply electrode positioned on a limb being measured;
b) a second current supply electrode on a second limb on a the same lateral side of the subject as the limb being measured;
c) a first voltage electrode positioned on a limb being measured; and,
d) a second voltage electrode positioned on a third limb contra-lateral to the limb being measured.

Typically the processing system is coupled to a measuring device, and wherein the method includes, in the processing system:
a) generating instructions; and,
b) transferring the instructions to the measuring device, the measuring device being responsive to the instructions to cause the impedance measurements to be performed.

Typically the processing system forms part of a measuring device.

Typically the measuring device includes at least two channels, each channel being adapted to measure the impedance across a respective body segment, and wherein the method includes, in the processing system, causing at least one impedance measurement to be performed using each channel.

Typically the measuring device includes a processor, and wherein the processor is for:
a) receiving the instructions; and,
b) causing one or more impedance measurements to be performed using the instructions.

In a second broad form the present invention provides apparatus for detecting tissue oedema in a subject, the apparatus including a processing system for:
a) determining a measured impedance value for at least one body segment;
b) for each body segment, and using the measured impedance values, determining at least one indicator, the indicator being at least partially indicative of a level of extracellular fluid;
c) determining an indication of the hydration status using at least one determined indicator.

Typically the apparatus includes:
a) a current supply for generating an alternating current at each of a plurality of frequencies;
b) at least two supply electrodes for applying the generated alternating current to a subject;
c) at least two measurement electrodes for detecting a voltage across the subject; and,
d) a sensor coupled to the measurement electrodes for determining the voltage, the sensor being coupled to the processing system to thereby allow the processing system to determine the measured impedances.

Typically the apparatus is adapted to perform the method of the first broad form of the invention.

In a third broad form the present invention provides a method for use in dialysis of a subject, the method including, in a processing system:
 a) determining one or more impedance values for at least one body segment;
 b) for each body segment, and using the measured impedance values, determining at least one indicator; and,
 c) selectively controlling the dialysis the subject using at least one determined indicator.

It will be appreciated that the broad forms of the invention may be used individually or in combination, and may be used in performing or controlling dialysis in subjects such as humans.

BRIEF DESCRIPTION OF THE DRAWINGS

An example of the present invention will now be described with reference to the accompanying drawings, in which:—

DETAILED DESCRIPTION OF THE PREFERRED EMBODIMENTS

Figure 1:
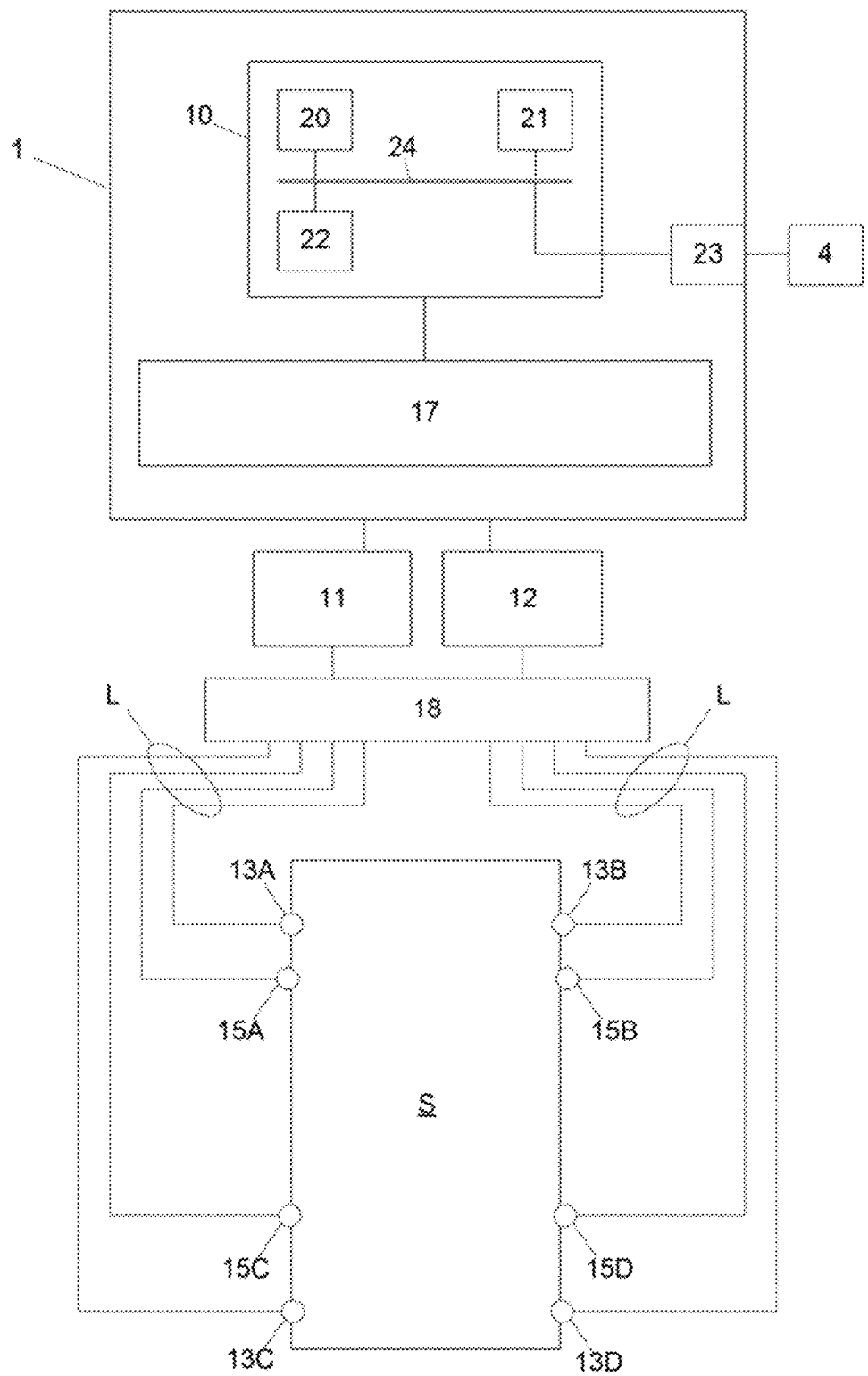
FIG. 1 is a schematic of an example of impedance determination apparatus.

An example of apparatus suitable for performing an analysis of a subject's impedance will now be described with reference to FIG. 1.

As shown the apparatus includes a monitoring device 1 including a processing system 10 having a processor 20, a memory 21, an input/output (I/O) device 22, and an optional external interface 23, coupled together via a bus 24. The external interface can be used to couple the measuring device 1 to one or more peripheral devices 4, such as an external database or computer system, barcode scanner, dialysis machine, any other required sensors, or the like. The processing system 10 is coupled to a signal generator 11 and a sensor 12, via a processing module 17, as shown.

In use the signal generator 11 and the sensor 12 are selectively coupled to respective electrodes 13A, 13B, 13C, 13D, 15A, 15B, 15C, 15D provided on a subject S, via a multiplexer 18, and connecting leads L, as shown.

The processing system 10 and processing module 17 are adapted to generate control signals, which cause the signal generator 11 to generate one or more alternating signals, such as voltage or current signals. These signals are then transferred to a selected pair of electrodes 13A, 13B, 13C, 13D by the multiplexer 18, allowing the alternating signals to be applied across a respective segment of the subject S, depending on the position of the selected pair of electrodes 13A, 13B, 13C, 13D. The sensor 12 is then connected to selected ones of the electrodes 15A, 15B, 15C, 15D, using the multiplexer 18, allowing the voltage across or current through the respective segment of the subject S to be measured. The processing system and processing module 17 are adapted to generate control signals to control the switching of multiplexer 18.

The sensor 12 transfers appropriate signals to the processing system 10, allowing the impedance of the respective segment of the subject S to be determined, as will be described in more detail below.

In any event, by using the multiplexer to selectively connect different pairs of the electrodes 13A, 13B, 13C, 13D to the signal generator 11, and pairs of the electrodes 15A, 15B, 15C, 15D to the sensor 12, this allows the impedance across different segments of the subject S to be measured. In general, the use of a particular combination of electrodes for measuring a particular body segment is referred to as a channel, and accordingly, it will be appreciated that the above described apparatus provides multi-channel functionality, allowing different body segments to be measured through appropriate switching of the multiplexer. However, multi-channel functionality may be achieved using other configurations, such as by providing a respective processing module 17, signal generator 11 and sensor 12 for each channel.

In any event, the processing system 10 may be any form of processing system which is suitable for generating appropriate control signals and interpreting voltage data to thereby determine the subject's bioelectrical impedance, and optionally the subject's dry mass to aid in dialysis.

The processing system 10 may therefore be a suitably programmed computer system, such as a laptop, desktop, PDA, smart phone or the like. Alternatively the processing system 10 may be formed from specialised hardware. Similarly, the I/O device may be of any suitable form such as a touch screen, a keypad and display, or the like.

Similarly, the processing module 17 is adapted to perform specific processing tasks, to thereby reduce processing requirements on the processing system 10. Accordingly, the processing module may be custom hardware, or the like, and in one example is formed from a Field Programmable Gate Array (FPGA), although any suitable processing module, such as a magnetologic module, may be used.

It will be appreciated that the processing system 10, the processing module 17, the signal generator 11, the sensor 12 and the multiplexer 18 may be integrated into a common housing and therefore form an integrated device. Alternatively, the processing system 10 may be connected to the signal generator 11 and the sensor 12 via wired or wireless connections. This allows the processing system 10 to be provided remotely to the signal generator 11 and the sensor 12. Thus, the signal generator 11 and the sensor 12 may be provided in a unit near, or worn by the subject S, whilst the processing system is situated remotely to the subject S.

Once the electrodes 13A, 13B, 13C, 13D are positioned, an alternating signal is applied to the subject S using a selected pair of the electrodes 13A, 13B, 13C, 13D. This may be performed either by applying an alternating signal at a plurality of frequencies simultaneously, or by applying a number of alternating signals at different frequencies sequentially. However the frequency range of the applied signals will also depend on the analysis being performed.

In the preferred implementation the applied signal is a frequency rich current from a current or voltage source, clamped or limited, so it does not exceed the maximum allowable subject auxiliary current. The signal can either be an impulse function or a voltage signal where the current is measured so it does not exceed the maximum allowable subject auxiliary current.

A potential difference and/or current is measured between a pair of the electrodes 15A, 15B, 15C, 15D.

To ensure accurate measurement of the impedance, buffer circuits are placed in connectors that are used to connect the voltage sensing electrodes 15 to the leads L. This ensures accurate sensing of the voltage response of the subject S, and in particular helps eliminate contributions to the measured voltage due to the response of the leads L.

This in turn greatly reduces artefacts caused by movement of the leads L, which is particularly important during dialysis as sessions are usually last for several hours and the subject will move around and change seating positions during this time.

A further advantage of this configuration is that the voltage is measured differentially, meaning that the sensor used to measure the potential at each electrode 15 only needs to measure half of the potential as compared to a single ended system. This in turn reduces the potential across the multiplexer 18, thereby greatly reducing capacitive leakage in the multiplexer, resulting in a corresponding increase in accuracy.

The current measurement system may also have buffers placed in the connectors between the electrodes 13 and the leads L. In this instance, current is also driven or sourced through the subject S symmetrically, which again greatly reduced the parasitic capacitances by halving the common-mode current. Another particular advantage of using a symmetrical system is that the micro-electronics built into the connectors for each electrode 13 also reduces parasitic capacitances that arise when the subject S, and hence the leads L move.

In any event, the acquired signal and the measured signal will be a superposition of potentials generated by the human body, such as the ECG, and potentials generated by the applied current.

Optionally the distance between the inner pair of electrodes 15A, 15B, 15C, 15D may be measured and recorded. Similarly, other parameters relating to the subject may be recorded, such as the height, weight, age, sex, health status, any interventions and the date and time on which they occurred and other information, such as current medication, may also be recorded.

The acquired signal is demodulated to obtain the impedance of the system at the applied frequencies.

One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a processing technique such as multiplying the measured signal with a reference sine wave and cosine wave derived from the signal generator and integrating over a whole number of cycles. This process totally rejects any harmonic responses and significantly reduces random noise.

Other suitable digital and analog demodulation techniques will be known to persons skilled in the field.

Impedance or admittance measurements are determined from the signals at each frequency by comparing the recorded voltage and current signal. The demodulation algorithm will produce an amplitude and phase signal at each frequency.

Figure 2:
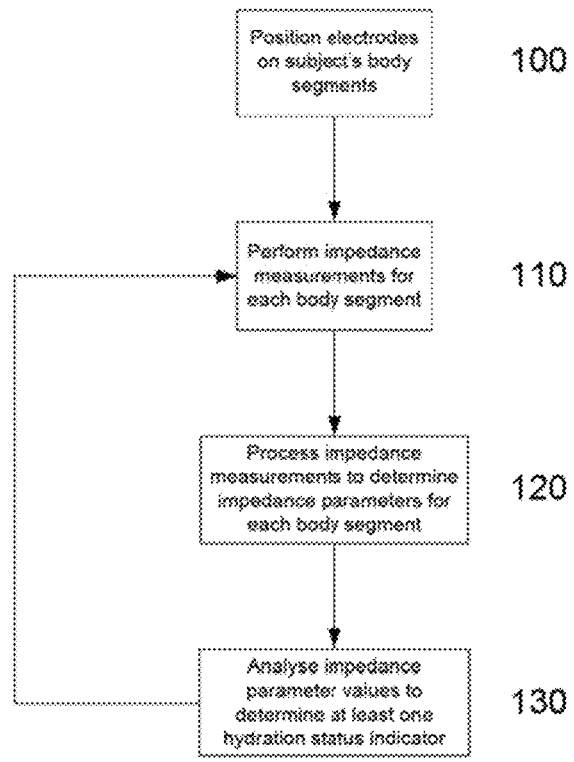
FIG. 2 is a flowchart of an example of an outline of a process for determining indicators of hydration status.

An example of the process of performing impedance measurements and determining indicators of hydration status utilising the apparatus to FIG. 1 will now be described with reference to FIG. 2.

At step 100 an operator of the apparatus positions electrodes 13, 15 on the subject before connecting leads to the electrodes 13, 15 so as to allow the apparatus to measure the impedance of a number of different body segments independently.

This will typically involve having the operator place a number of electrodes 13, 15 on the subject S and then connecting leads between the electrodes 13, 15 and the multiplexer 18 to allow the measuring device 1 to determine the impedance of respective body segments by selectively making measurements via the various channels.

At step 110 the measuring device 1 will operate to perform impedance measurements by generating an appropriate current sequence and applying this to the subject S via a pair of the electrodes 13A, 13B, 13C, 13D. This is typically performed in sequence for each channel, thereby allowing measurements to be determined for each body segment in turn.

At step 120 the measuring device 1 operates to process the impedance measurements so as to determine impedance parameters for each body segment, which can then in turn be analysed to determine indicators of the subject's current hydration status.

This process will now be described in more detail with respect to FIGS. 3A and 3B, and with reference to the graphical user interface (GUI) screen shots shown in FIGS. 4, 5, 6 and 7.

Figure 3A:
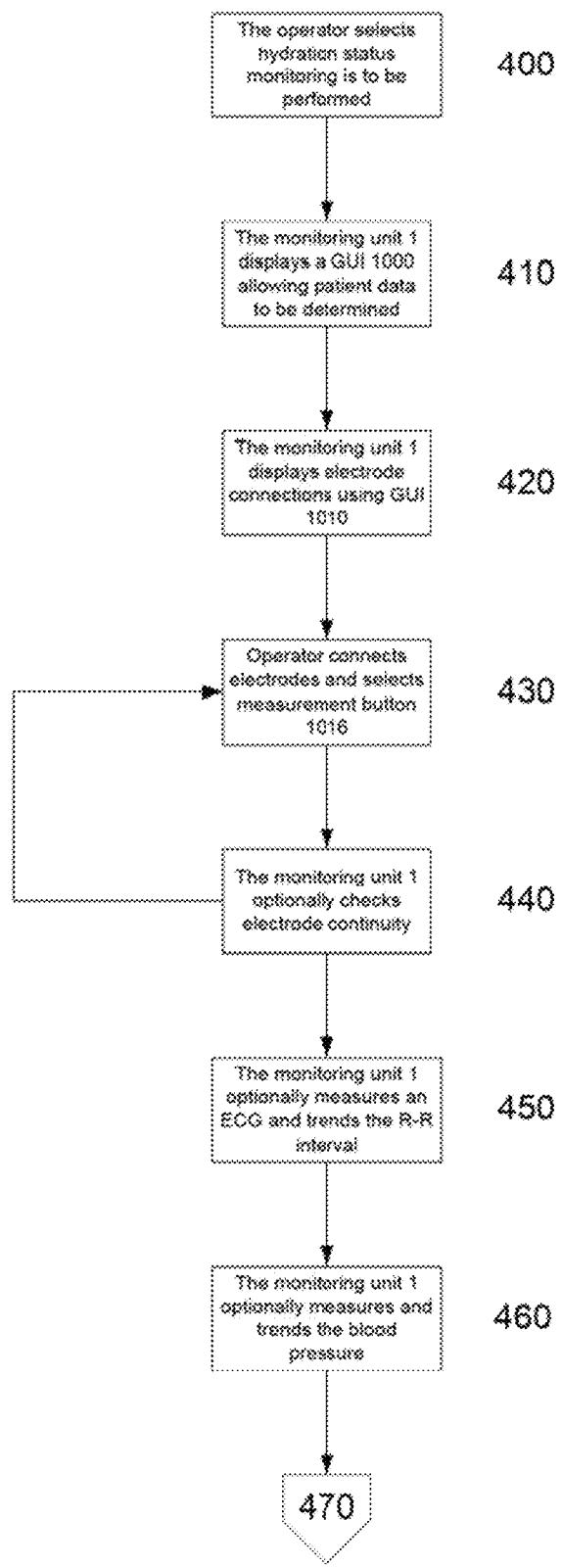
FIGS. 3A and 3B are a flow chart of an example of a detailed process for determining indicators of hydration status.
Figure 3B:
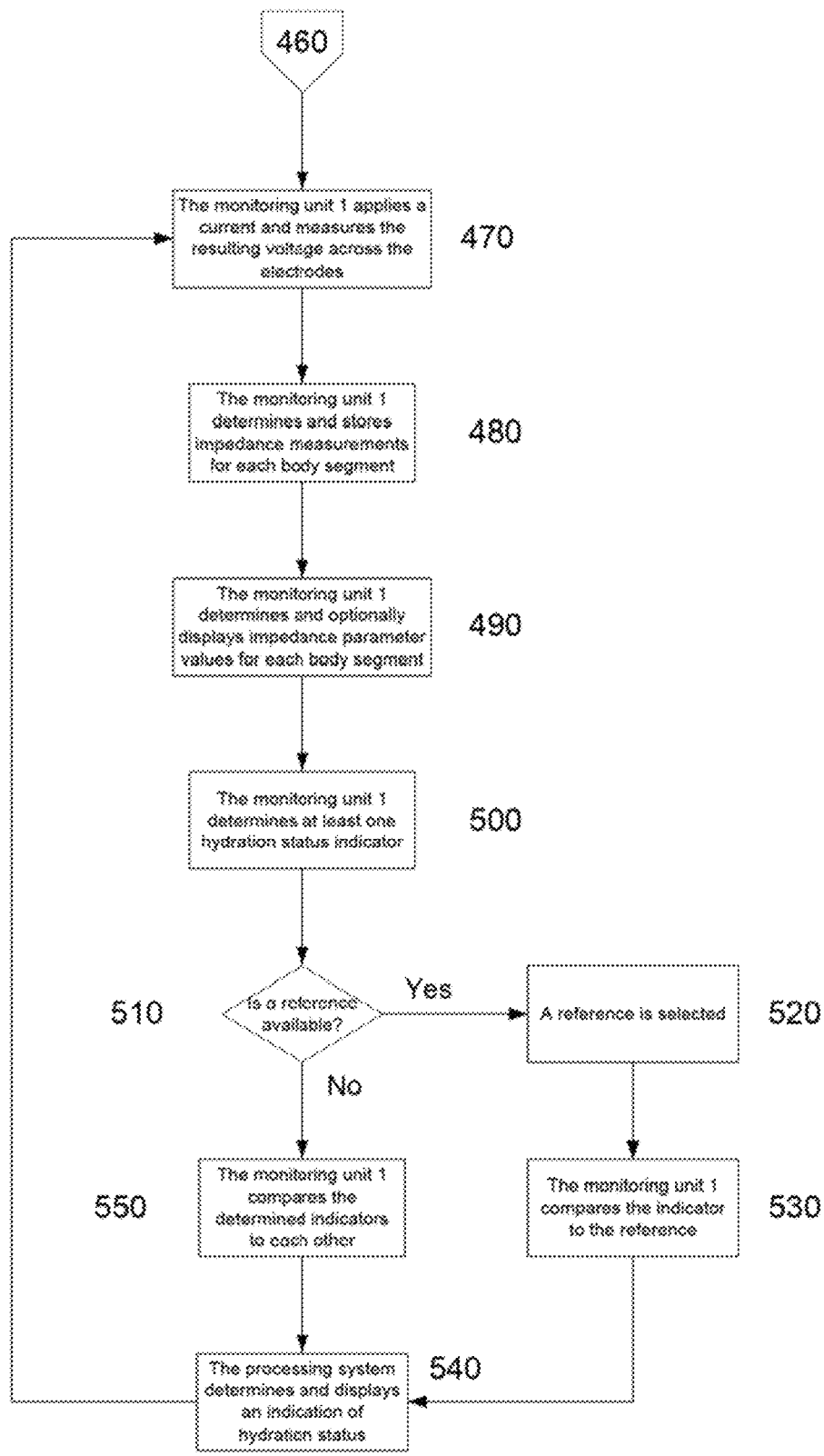

In the example set out in FIG. 3A at step 400 the operator selects that hydration status monitoring is to be performed. This may be required for example in the event that the measuring device 1 is able to perform a number of different types of measurement procedure, and typically involves having an operator select hydration status monitoring from a list of available measurement types. The available measurement types are typically determined by the processing system 10 either from the memory 21, or alternatively downloaded via the external interface 23 and are based on predetermined profiles which provide suitable instructions to allow the measuring device 1 to perform the required impedance measurements.

At this stage, the processing system 10 may download appropriate firmware into the FPGA 17, allowing the correct impedance measurement process to be performed by the FPGA.

Figure 4A:
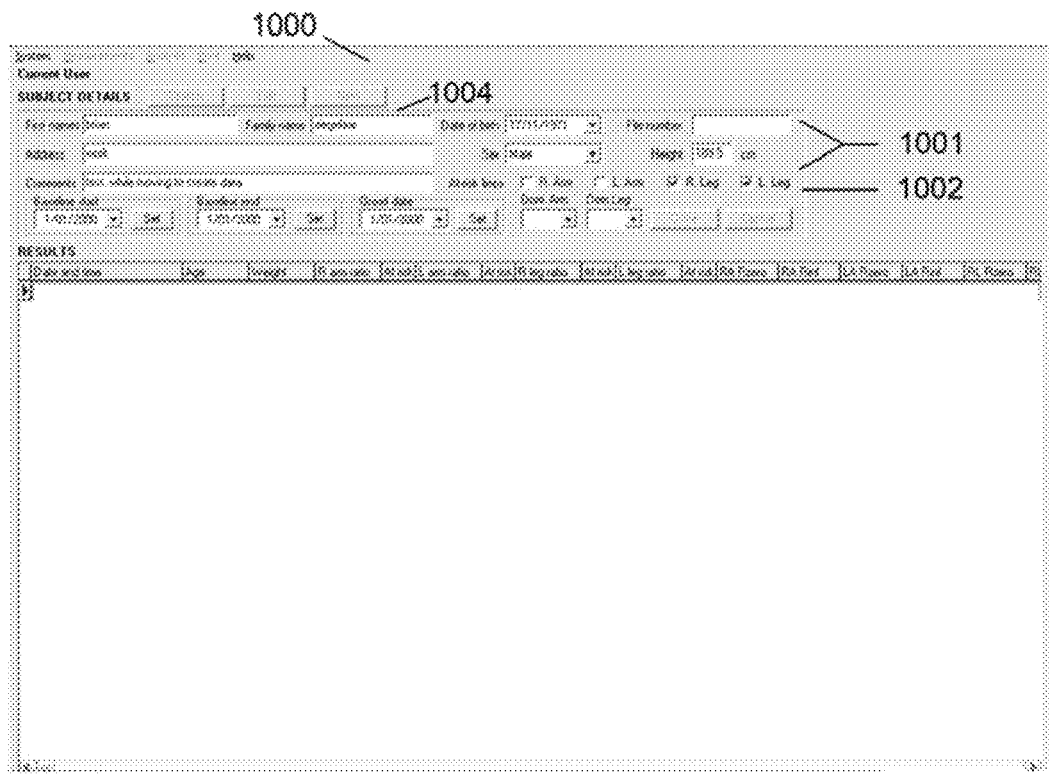
FIGS. 4A and 4B are examples of a GUI used in providing subject details.

At step 410 the measuring device 1 displays a GUI 1000 as shown in FIG. 4A. The GUI includes a number of fields, shown generally at 1001, which allow data regarding the individual to be provided. The data includes information such as name, address, sex, height, weight, limb length or the like. Additionally, an indication of limbs at risk from oedema can be input as shown at 1002, as this can be used in assisting with the analysis.

This is used to create a subject record, which is typically stored in a subject database accessed via the external interface 23, or the like. The subject record includes the subject data, and details of any performed impedance measurements for the respective subject, thereby allowing the subject record to form a subject history for use in longitudinal analysis. Thus, it will be appreciated that in the event that a record already exists for the current subject, then the operator can perform a search to retrieve the record from the database. The database is typically a HL7 compliant remote or local database.

In one example, the subject can be provided with a wristband or the like which includes coded data indicative of the subject identifier. In this case, the measuring device 1 can be coupled to a peripheral device 4 for determining the subject identifier. Thus, for example, the data may be in the form of a barcode, with the peripheral device 4 being a barcode scanner. It will be appreciated however that any suitable mechanism could be used for encoding the subject identifier such as RFID (Radio Frequency ID) tags could be used, in which case the peripheral device will be a corresponding reader.

In this example, the barcode reader detects the barcode provided on the subject's wrist band, and determines a subject identifier from the detected barcode. The barcode reader provides data indicative of the sensed subject identifier to the processing system 10, thereby allowing the processing system 10 to access the subject record from the database.

Alternatively however the subject identifier could be entered manually by an operator, for example, by using the I/O device 22.

In the event that information such as limb length is not available then the measuring device 1 can estimate these from other subject data, such as a the subject height, using anthropometric tables, or the like. These can be customised by the operator of the measuring device, or can be downloaded from a central repository such as the database.

Figure 4B:
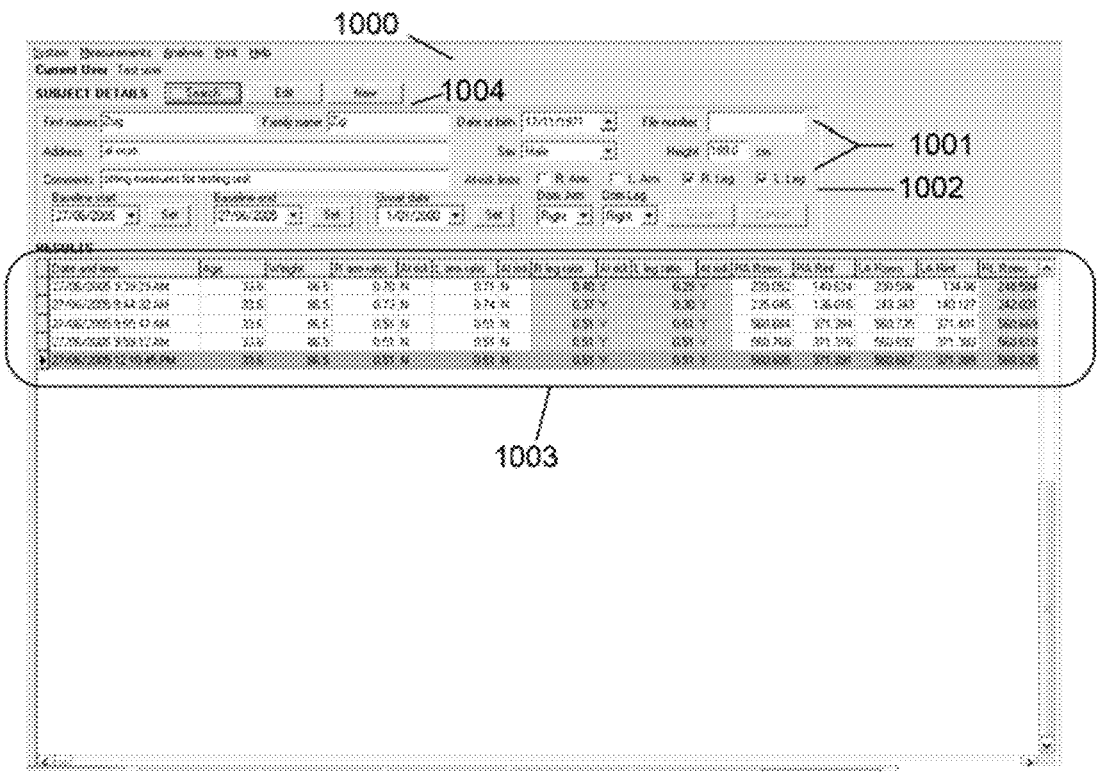

In any event, once this information is provided or otherwise determined, the processing system will update the GUI 1000 as shown in FIG. 4B to display any previously measured impedance values, which may be used as reference data, as will be described in more detail below. Searching, editing and creation of records using the input controls shown generally at 1004.

Figure 5A:
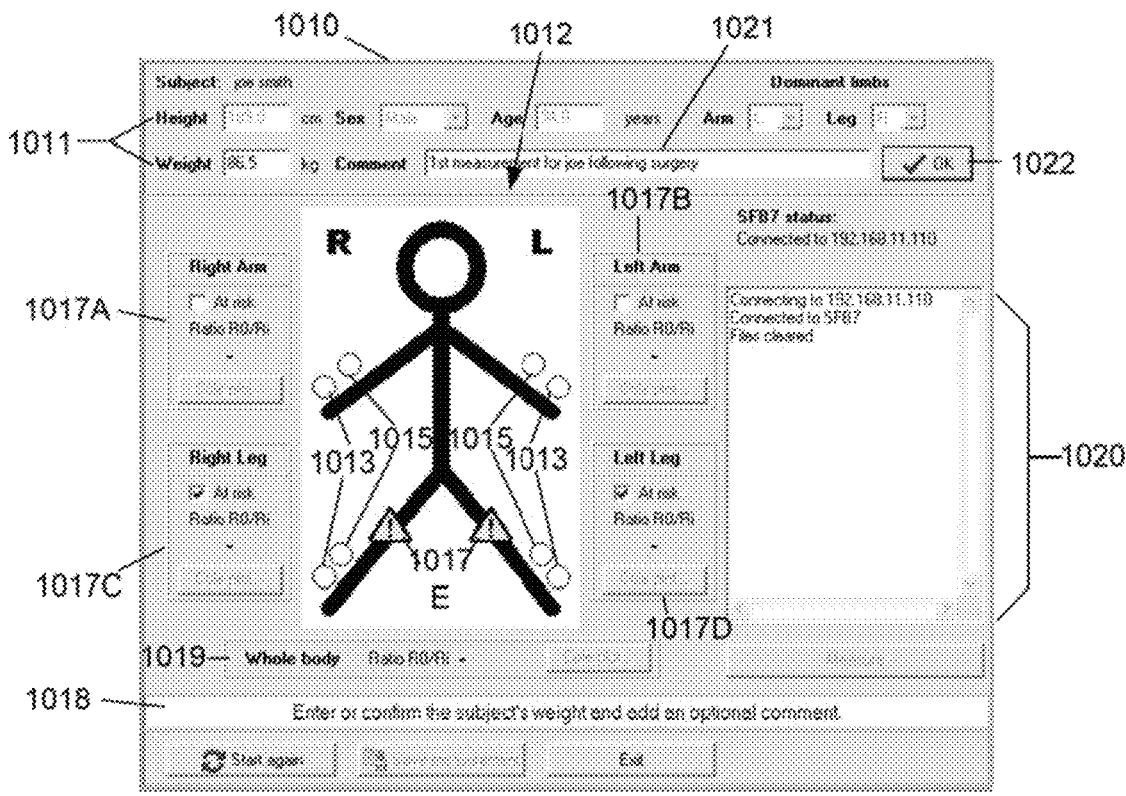
FIG. 5A is an example of a GUI used in providing electrodes on a subject.

At step 430 the processing system 10 generates a GUI 1010, an example of which is shown in FIG. 5A, and which is used in allowing the operator to provide electrode connections. In this example, the GUI 1010 includes an indication of subject details at 1011. A representation 1012 of the subject is provided, which shows general electrode connection points 1013, 1015, indicating where on the subject electrodes 13, 15 should be provided.

Figure 5B:
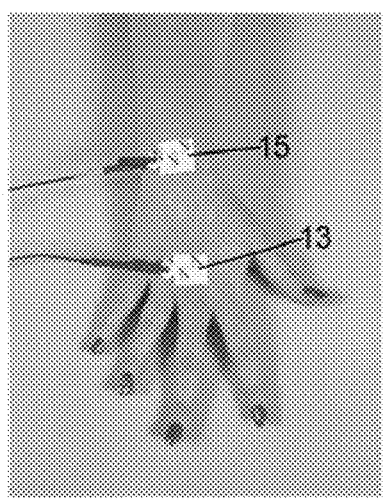
FIGS. 5B and 5C are examples of typical electrode placements.
Figure 5C:
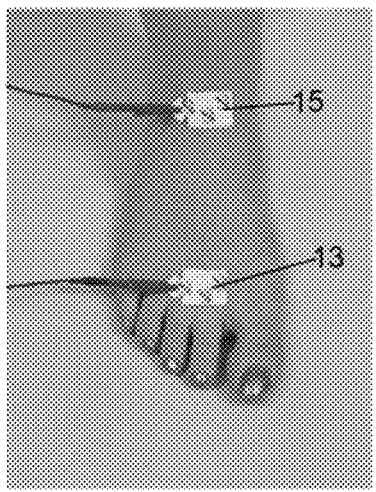

The general arrangement is to provide electrodes on the hand at the base of the knuckles and between the bony protuberances of the wrist, as shown in FIG. 5B, and on the feet at the base of the toes and at the front of the ankle, as shown in FIG. 5C.

Figure 5D:
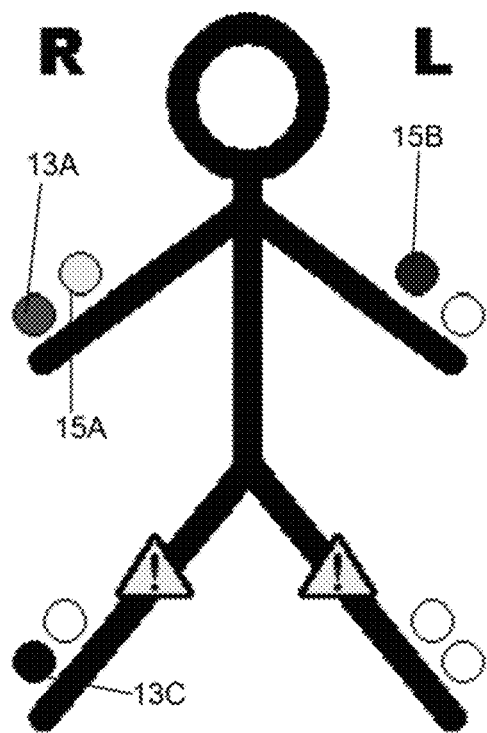
FIG. 5D is an example of an electrode configuration used in measuring the impedance of a subject's right arm.
Figure 5E:
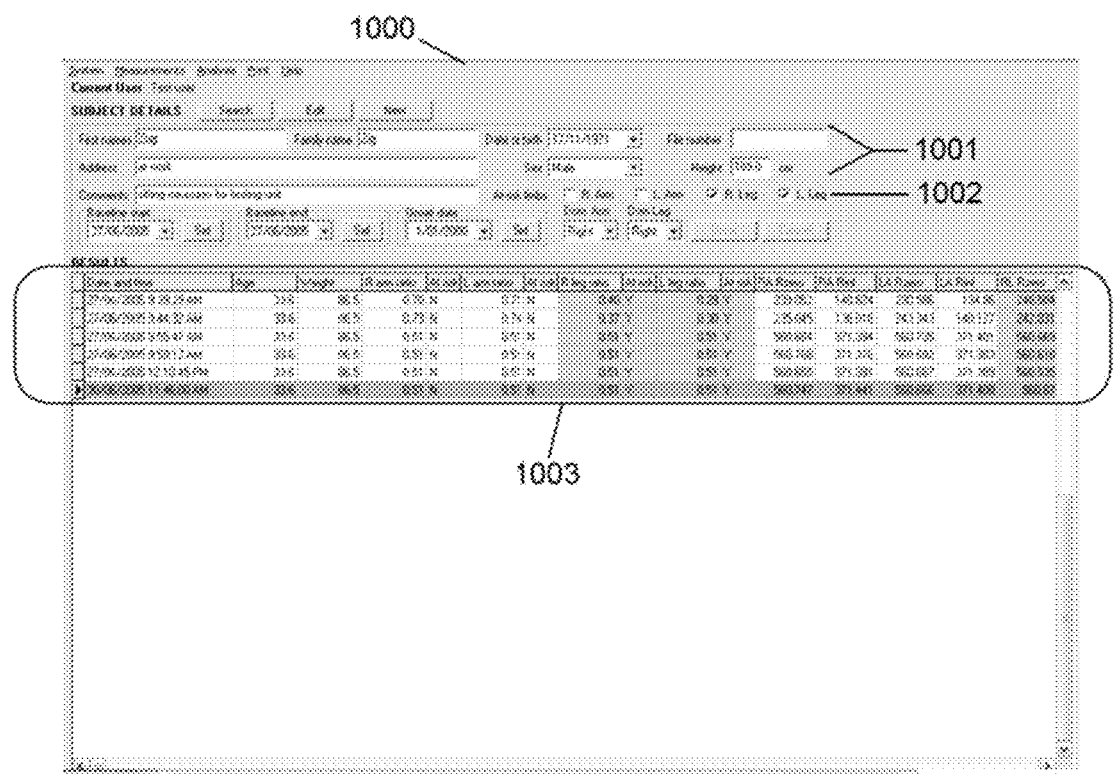
FIG. 5E is an example of a GUI used in performing impedance measurements.

It will be appreciated that this configuration uses the theory of equal potentials, allowing the electrode positions to provide reproducible results for impedance measurements. For example, when one of the channels is being used to measure the impedance of the right arm, the electrode configuration used is as shown in FIG. 5D.

In this configuration, current is injected between electrodes 13A and 13C, with the electrodes 15A positioned as shown, and the electrode 15B being placed anywhere along the left arm, since the whole arm is at an equal potential. This is advantageous as it greatly reduces the variations in measurements caused by poor placement of the electrodes by the operator. It also greatly reduces the number of electrodes required to perform segmental body measurements, as well as allowing the limited connections shown to be used to measure each of limbs separately.

In one example, the current electrodes are provided on one hand and one foot, whilst the voltage electrodes are positioned a set distance apart on a calf or on a bicep. This is particularly advantageous as fluid levels in the calf are generally sensitive to changes in the subject's posture, whilst fluid levels in the bicep are relatively posturally invariant. Consequently, comparison of impedance measurements made at a subject's calf and bicep can be useful in detecting the subject's optimal fluid state, whilst taking into account changes in posture, as will be described in more detail below.

The GUI 1010 also displays details for each limb at 1017A, 1017B, 1017C, 1017D, including an indication of whether the limb is an at risk limb, which is a limb suffering from vascular insufficiency, as caused for example by surgery, obesity, an accident, or the like. An example of acquired vascular insufficiency is lymphoedema. This is also shown on the representation 1012 at 1017E.

An instruction field is shown generally at 1018 and this is provided to display instructions to the operator, with an indication of the selected measurement procedure being shown at 1019, and general measuring device status information being provided at 1020. A comments field 1021 can also be used to record comments regarding the measurements made.

At this stage the operator typically updates the weight of the subject in the subject details 1011, which may undergo significant variations over time due to changes in fluid levels within the subject's body. The operator may also re-specify the at risk limbs, which is useful when a subject develops further vascular insufficiency in a limb. For example, a subject may start off with unilateral vascular insufficiency of the left leg and over time may develop a vascular insufficiency in the right leg. This leg can be recorded at that point as being affected by the use of the "at risk" check boxes.

Once the weight and comments are entered the measurement procedure can be initiated by clicking the "ok button" 1022. At this stage, both the weight and comments for each measurement are recorded as part of the corresponding subject record in the subject database. This allows the practitioner to track weight and clinical comments over the period of measurement as well as between different measurement periods.

Thus, it will be appreciated from the following that the process can be used to measure the dry mass of the subject, not only during a dialysis session, but also between different dialysis sessions, thereby further enhancing the ability of the system to determine any deviation from optimal haemostasis conditions. The system can also be used to track additional information, relating to details of potential triggers, such as the subject's food and drink consumption. This coupled with the fact that the system can accurately determine indicators of dry mass and hydration status can be used with trigger information to assess which potential triggers have a material, and adverse effect on the subject and the dialysis process. This in turn allows the triggers to be avoided in future.

At step 440, the measuring device 1 optionally checks electrode continuity. This can be achieved based on the theory of equipotentials by comparing potentials measured at different ones of the electrodes. In particular, the process can measure the potential at different electrodes on a given limb, and these should be identical in accordance with the equipotential theory. In the event that the measured potentials are different, this indicates that there is a fault, such as a problem with the connection to one of the electrodes.

Additionally, or alternatively, it is possible to examine raw data from the applied current signal and the differential voltage signal, as acquired from the signal generator 11 and the sensor 12, and examine either the absolute magnitude of the signals, or a signal to noise ratio. In this instance, if either the absolute magnitude of the voltage signal, or the signal to noise ratio, are below respective thresholds, then this indicates a problem with the electrode connections.

Any problem with the electrode connections can be indicated to the operator of the measuring device 1 allowing the connection problem to be corrected.

If the electrode continuity is checked and it is determined the electrodes are not configured or working correctly, the process returns to step 430 so that the operator replaces or repositions the electrodes.

Otherwise, at step 450, the measuring device 1 optionally measures ECG signals. This can be achieved either through the use of a 5 lead ECG measurement process that utilises the same electrodes as used in measuring the impedance. Alternatively, optional additional leads may be used to allow for recording full 12 lead ECG measurements. If ECG signals are measured, these can be used to monitor an R-R interval trend using chaotic predictors. This can be used to determine a warning of the onset of a malignant or unstable arrhythmia, up to 10 minutes prior to the arrhythmia developing.

Additionally, this can be used to monitor cardiac output allowing a warning to be sounded when cardiac output starts to drop during dialysis. This may indicate that the patient will not have adequate cardiac function if more fluid is removed. This can be used to determine the optimum fluid loading for a patient suffering from cardiac disease who also requires dialysis.

At step 460, the measuring device 1 optionally measures and trends blood pressure signals.

At step 470, the measuring device 1 then performs the required impedance measurements, with general measuring device status information being provided at 1020. To achieve this, the monitoring device 1 applies the required current signals to one of the body segments, via a respective one of the channels A, B, measuring the resulting current and voltage across the body segment. This allows instantaneous impedance values to be determined at a number of different frequencies $f_i$, for the respective body segment, which are then stored at step 480.

The measuring device 1 repeats this for each of the measurement channels, so that impedance measurements are determined for each of the body segments separately.

At step 490 the measuring device 1 operates to determine impedance parameters for each body segment. Typically this includes parameters such as the impedance at zero, characteristic and infinite frequencies ($R_0$, $Z_c$, $R_\infty$). These can be derived based on the impedance response of the subject, which at a first level can be modeled using the equation (1):

$$Z = R_\infty + \frac{R_0 - R_\infty}{1 + (j\omega\tau)} \quad (1)$$

where: $R_\infty$=impedance at infinite applied frequency,
$R_0$=impedance at zero applied frequency,
$\omega$=angular frequency,
$\tau$ is the time constant of a capacitive circuit modeling the subject response.

However, the above represents an idealised situation which does not take into account the fact that the biological tissues are an imperfect system. Taking this into account leads to a modified model, called the Cole model, in which:

$$Z = R_\infty + \frac{R_0 - R_\infty}{1 + (j\omega\tau)^{(1-\alpha)}} \quad (2)$$

where $\alpha$ has a value between 0 and 1 and can be thought of as an indicator of the deviation of a real system from the ideal model.

The value of the impedance parameters $R_0$ and $R_\infty$ may be determined in any one of a number of manners such as by:
solving simultaneous equations based on the impedance values determined at different frequencies;
using iterative mathematical techniques;
extrapolation from a "Complex impedance plot" (also sometimes referred to as a "Wessel" or "Cole-Cole" plot) or argand diagram;
performing a function fitting technique, such as the use of a polynomial function.

At this stage the processing system 10 can also be adapted to test adherence of the measurements to the Cole model. In particular, the Cole model assumes that the impedance measurements lie on a semi-circular impedance locus. Accordingly, the processing system 10 can determine if the measured values fit a semi-circular locus to thereby determine if the Cole model is satisfied. Alternatively, the measured impedance parameter values can be compared to theoretical values derived using the equation (2), to thereby allow the degree of concordance to the Cole model to be determined.

In the event that the Cole model is not satisfied, an indication of this can be provided to the operator allowing an appropriate analysis technique to be utilised.

Once the parameters have been determined, these can optionally be viewed using a GUI, an example of which is shown in FIGS. 6A to 6D. In this example, the GUI 1030 includes subject details at 1031, and a measurement selection inputs 1032. This allows the operator to select measurements of interest, which in this example includes measurements from the left arm. Once the measurements are selected, the processing system 10 displays an overview of parameters determined from the impedance measurements at 1033.

Figure 6A:
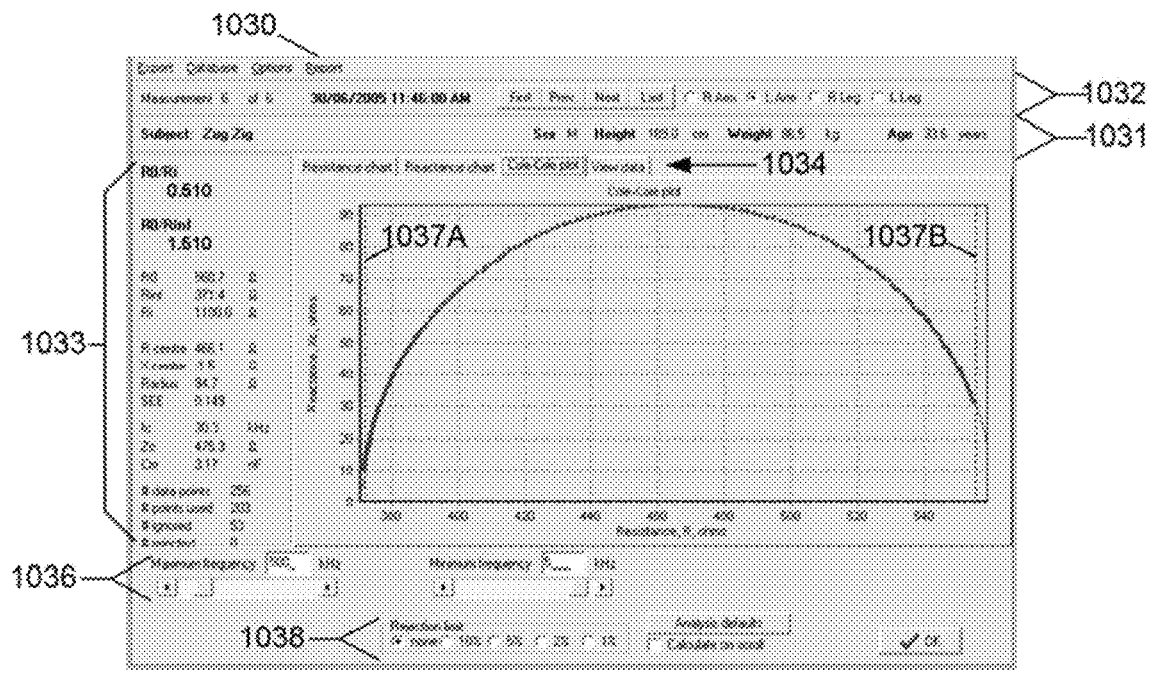
FIGS. 6A to 6D are examples of a GUI used in viewing measured impedance parameters.
Figure 6B:
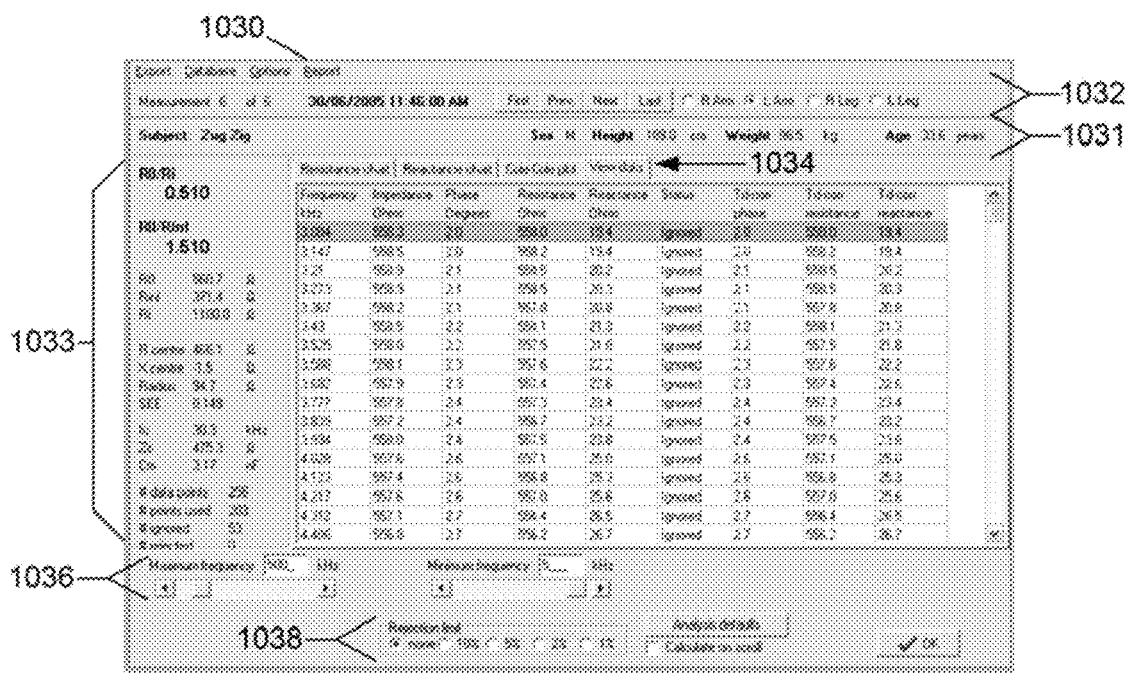
Figure 6C:
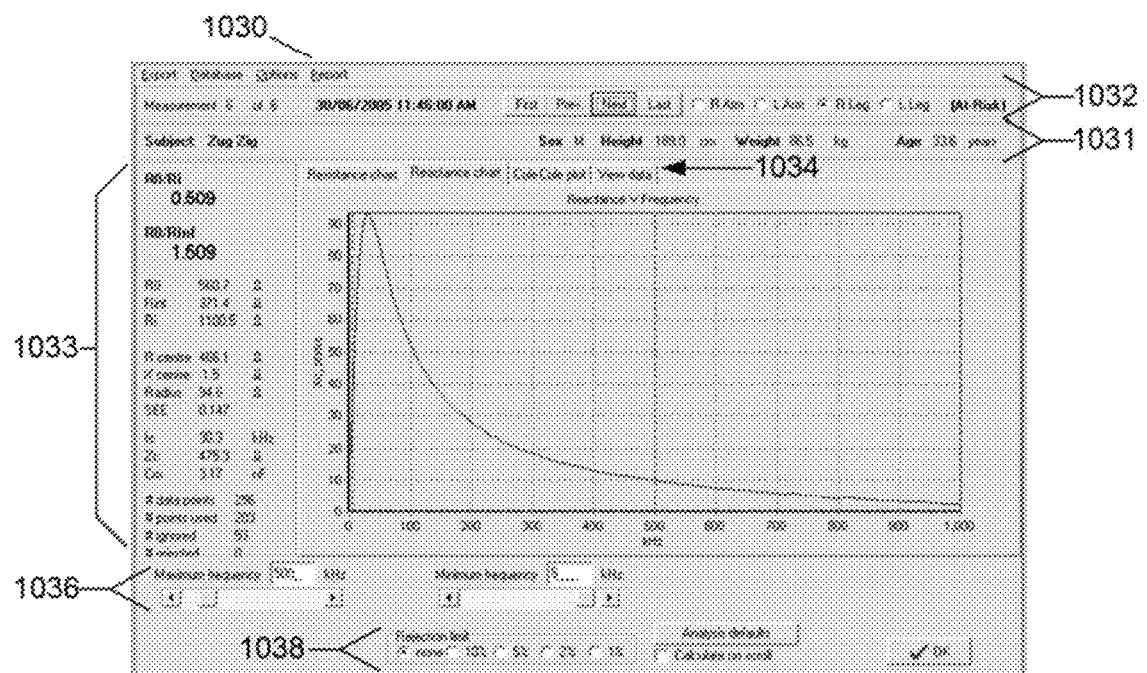
Figure 6D:
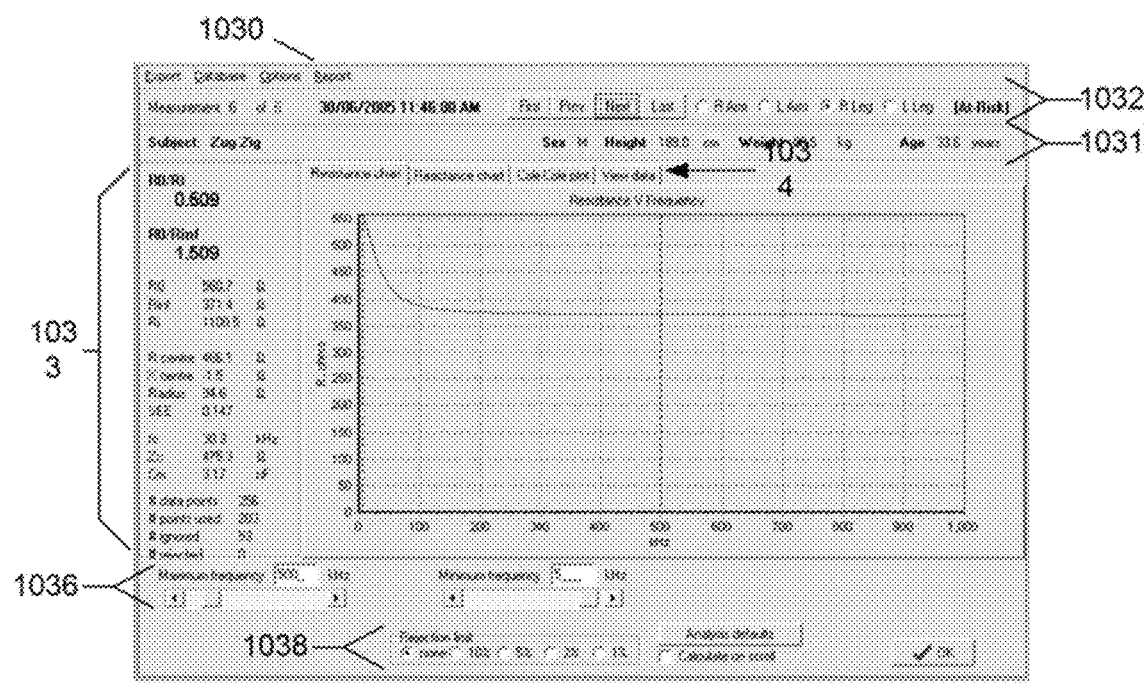

A number of tabs 1034 can then be used to allow different representations of the measured impedance values to be provided in a window 1035. This includes, for example, producing a complex impedance plot, as shown in FIG. 6A. Alternatively the impedance values can be listed as shown in FIG. 6B, or plotted as reactance verses frequency or resistance verses frequency as shown in FIGS. 6C and 6D respectively.

Frequency controls 1036 are provided to allow impedance measurements above or below threshold limits to be omitted from the displayed results, as shown by threshold markers 1037A, 1037B. Additionally a rejection limit can be applied to discard data points that fall outside a threshold variation from an idealised semi-circular locus provided on the complex impedance plot.

The impedance parameter values can then be analysed to derive indicators of hydration status.

In particular, as will be appreciated by persons skilled in the art, when a subject is undergoing dialysis, there is significant movement of fluid within the body. This can lead to an excess of extracellular fluid in some body segments, resulting in oedema, and/or a reduction in extracellular fluid in other body segments.

Accordingly, it is typical for the parameters to be used to derive indicators that are at least partially indicative of the extracellular fluid levels in each of the body segments and/or the entire body. The indicators are therefore typically indicative of the extracellular fluid volume, or an index based on the ratio of extra- to intra-cellular fluid.

In the case of the extracellular fluid volume, this can be calculated for each body segment using the equation:

$$ECV_{Segment} = C_{Segment}\rho_{Segment}\left(\frac{L_{Segment}^2}{R_{Segment}}\right) \quad (3)$$

Where ECV=Extracellular fluid volume
$C_{Segment}$=Geometry Constant which is 1 for an arm or leg and 4 for the thoracic cavity
$L_{Segment}$=Length of the segment in cm
$R_{Segment}$=Resistance of the segment in Ohm
$\rho_{Segment}$=Resistivity coefficient which is nominally 47 Ohm/cm The resistivity coefficient can be determined at each moment by using a nominal population reference where alpha is measured and then a corresponding resistivity for extracellular fluid is determined. This can also be done using all the variables from a model such as the Cole model to determine the appropriate resistivity. Alternatively this can be manually entered or measured using techniques known to persons skilled in the art.

The total body fluid is calculated according to:

$$ECV_{Total} = 2(ECV_{arm} + ECV_{leg}) + ECV_{trunk} \quad (4)$$

The extracellular fluid resistance $R_e$ is determined from:

$$R_e = R_0$$

and intracellular fluid resistance $R_i$ is determined from:

$$R_i = \frac{R_\infty R_e}{R_e - R_\infty}$$

Thus, this can be used to derive an index I, which is indicative of the ratio of extra- to intra-cellular fluid is given by the equation:

$$I = \frac{R_i}{R_e} = \frac{R_\infty}{R_0 - R_\infty} \quad (5)$$

Figure 8:
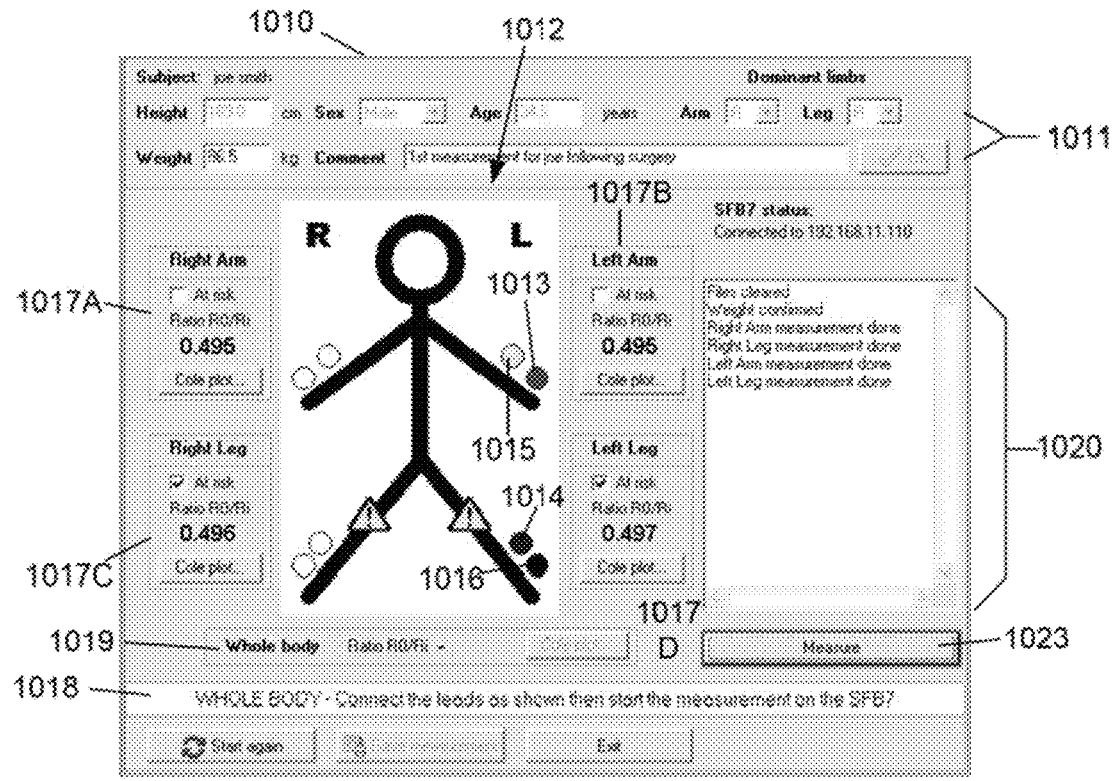
FIG. 8 is an example of a GUI used in performing total body impedance measurements.

Additionally, the total body water can also be used as an indicator for hydration status. In this example, by positioning the electrodes as shown in FIG. 8, this allows impedance measurements across the subject's entire body to be determined. This in turn allows the subject's total body water (TBW) to be derived given by:

$$TBW = ecf + icf \quad (6)$$

where: TBW=total body water
ecf=volume of extracellular fluid
icf=volume of intracellular fluid In this regard, the volumes of extracellular and intracellular fluid can be derived from the values $R_0$, $R_\infty$, as these depend on the values of the extracellular and intracellular resistance, as discussed above.

The analysis of the extracellular fluid volumes, the index I and/or the total body water may be achieved in a number of ways, but typically involves comparing the parameters to available references, and accordingly, the process determines if references are available at step 510. If references are available, the measuring device 1 allows the user to select an appropriate reference at step 520.

For example, the reference can be in the form of earlier data collected for the respective subject, thereby allowing a longitudinal analysis to be performed. This typically requires that data are collected prior to dialysis or other interventions, allowing the measuring device 1 to determine if there are any variations in the subject's extracellular fluid levels during the dialysis process, thereby indicating a change in subject hydration status. This can be performed for each body segment separately, or for the entire body.

However, the system may also or alternatively use a normal population database table, which includes reference values obtained from different subjects. This database table is essentially a single subject database table into which all measurements of normal population subjects (people without vascular insufficiency) are added.

Figure 7A:
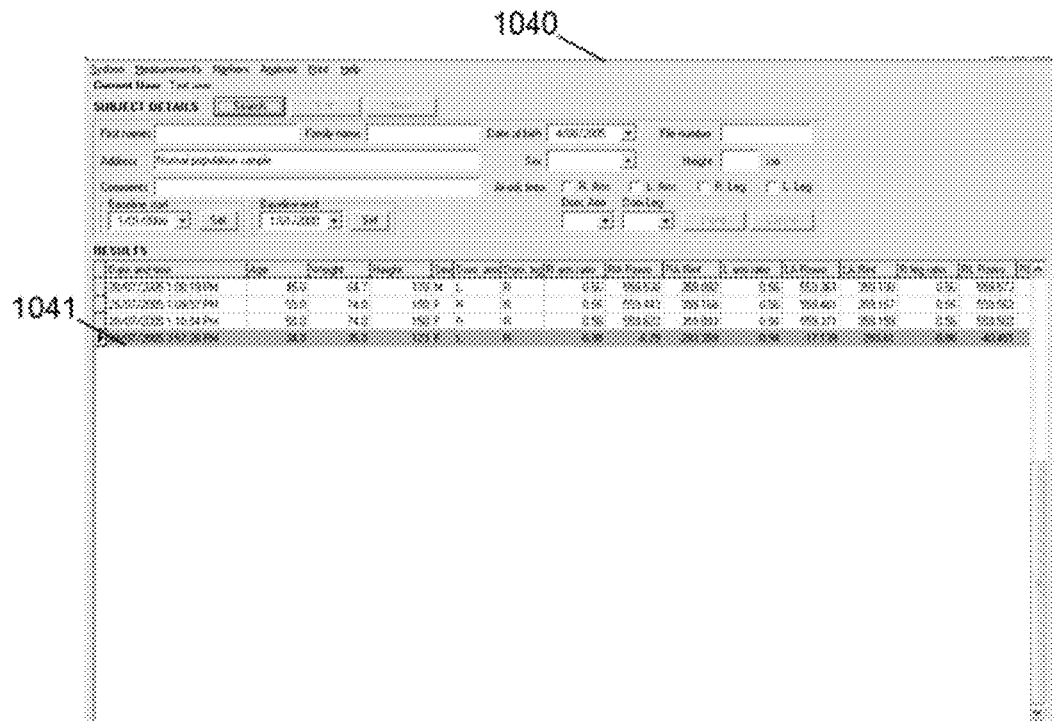
FIGS. 7A and 7B are examples of a GUI used in selecting references.

An example of such normal population data displayed using the GUI 1000 is shown in FIG. 7A. This table then acts as a pool of data from which normalised values for raw impedance data and ratios of impedance data can be generated, allowing comparison with measured values for the subject to be performed.

This generation of this normalised data is in the form of mean (averaged) values that are selected to be relevant to the test subject. The selection is performed based on the subject information and may be performed on the basis of any one of a number of factors, such as age, sex, height, weight, race, interventions, or the like.

Therefore if the test subject is female then the normalised data drawn from the normal population database will be calculated from measurements from female subjects that are present in the in the normal population database.

Thus, in one example, the operator is presented with the GUI 1040 similar to that shown in FIG. 7A, which allows the operator to select appropriate records from the normal population table, as shown by the highlighted entry at 1041.

It will be appreciated that the normalised population references are generally less accurate than subject specific references as these do not necessarily accurately model the subject's fluid levels and hence hydration status prior to undergoing dialysis.

In the case of using a subject specific reference, this is generally achieved by ensuring measurements taken prior to surgery, requiring dialysis, interventions, heart disease, or other events that will have an impact on the hydration status. Thus, for example, if the subject is undergoing dialysis, then the reference can be formed from parameter values derived prior to commencement of the dialysis procedure.

A common example is baseline measurements taken before surgical intervention for breast cancer that can be used to track subjects fluid shifts post surgery by comparison of study measurements to these baseline generated mean values.

Subject specific baselines can be generated automatically from measurements in the subject's database table. This can in turn be used to provide cut off points for dialysis based on when the measured impedance values or derived indicators approach predetermined impedance or indicator values representing an ideal or optimal fluid level or hydration status.

Figure 7B:
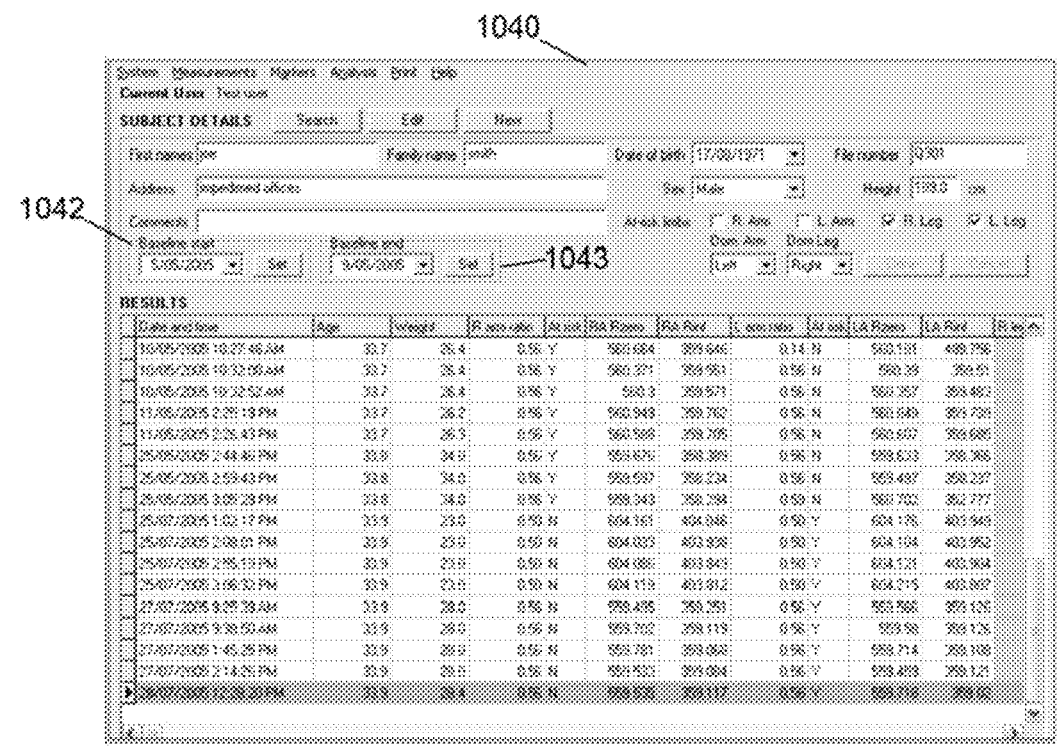

Generation of baselines can be achieved using the GUI 1000 shown in FIG. 7B, in which the subject's record is displayed. Located on the GUI 1000 are two selection windows 1042, 1043 that are used to define the measurements used from the subject's database table to generate mean data values for comparison to study measurements.

It will be appreciated that the process can also be used to add data to the normal population table. This is achieved by performing the measurement process outlined above, and in the event that the subject is healthy, or the subject is a control, such as a family member, importing the data into the normal population table. This can be performed in addition to adding the measurements to the subject record, so that measurements collected from a healthy individual can be used for subsequent longitudinal analysis and/or as a normal population reference.

In any event, once an appropriate reference is selected at step 520, the measuring device 1 compares the currently determined indicator to the reference at step 530, and utilises this to generate an indication of the hydrations status which is then displayed at step 540.

If no reference is available, the indicators determined for each body segment are compared to the indicators determined for other ones of the body segments. This allows a relative distribution of fluid within the subject to be monitored, which in turn allows an indication of hydration status to be determined.

For example, this can be used to determine the presence or absence of oedema. In the event that it is believed that the subject has one or more limbs at risk of oedema (i.e. suffering from vascular insufficiency of that limb), then the onset of oedema is in turn indicative of variations in the subject's hydration status. In this instance, the analysis of each of the limbs will be influenced by whether the subject is deemed to be at risk of bilateral oedema (i.e. suffering from vascular insufficiency of two limbs).

In particular, if there is no risk of bilateral oedema, then the processing system 10 can compare parameters for contra-lateral limbs. This may be achieved for example by determining an index based on a ratio of the extra- to intra-cellular fluid levels in each leg, and then comparing the values determined to assess whether there is difference between the limbs, or against a reference value for that limb, and hence whether there is a likelihood of oedema being present.

In the event that there is a likelihood of the vascular insufficiency being bilateral, then the processing system 10 typically determines the index for each limb. A ratio of the determined index I for different pairs of limbs are then compared, thereby allowing the operator to determine if there is a likelihood of bilateral oedema.

In any event, it can be seen that if there is a major variation in the extracellular fluid volume, or the index I, either over time in the case of longitudinal analysis (either extending through a dialysis session, or extending over multiple sessions), compared to normal references, or between different body segments, this is indicative of a changing hydration status. This is in turn indicative of the fact that the dialysis procedure needs to be modified in order to counteract this change, and ensure that the subject is correctly hydrated.

Accordingly, the measuring device 1 can use this to display a report that is indicative of the hydration status, and/or the presence, absence or degree of oedema.

However, as an alternative to the above described process, the hydration status can be monitored by examining other indicators, such as by examining the impedances values at different selected frequencies.

Thus, for example, this may involve calculating impedance values at specific frequencies in the complex impedance plot. This may include theoretical impedance values such as $R_0$ and $R_\infty$, vectors representing the actual measured values, or theoretical values derived at set frequencies, as well as the difference between values of $R_0$ and $R_\infty$.

In one example, the process set out in steps 510 to 540 can involve repeatedly making measurements during the dialysis procedure, and then monitoring the variation in one or more of the above mentioned indicators, such as the value of $R_\infty$, the level of extra-cellular fluid, the index I, or the like.

In this example, as dialysis proceeds, fluid levels within the subject's body should alter, resulting in a corresponding alteration of the indicator. As the dialysis procedure reaches a desired end point and fluid levels within the subject approach an ideal or optimal level, this will also result in a corresponding stabilisation of the indicators. Accordingly, in one example, the process involves monitoring for variation, and in particular, a rate of change of the indicators. When the rate of indicator variation falls below a predetermined threshold, this indicates that the value of the indicator, and hence patient fluid levels, have substantially stabilised, thereby allowing the dialysis procedure to be halted.

Thus, in one example, the process involves monitoring changes in the values of indicators such as $R_0$, $R_\infty$, the difference between $R_0$ and $R_\infty$, vector impedance values, or any other indicator, and then using the rate of variation to control the dialysis process.

Examples of the different types of available reports will now be described with reference to FIGS. 7C to 7I.

Figure 7C:
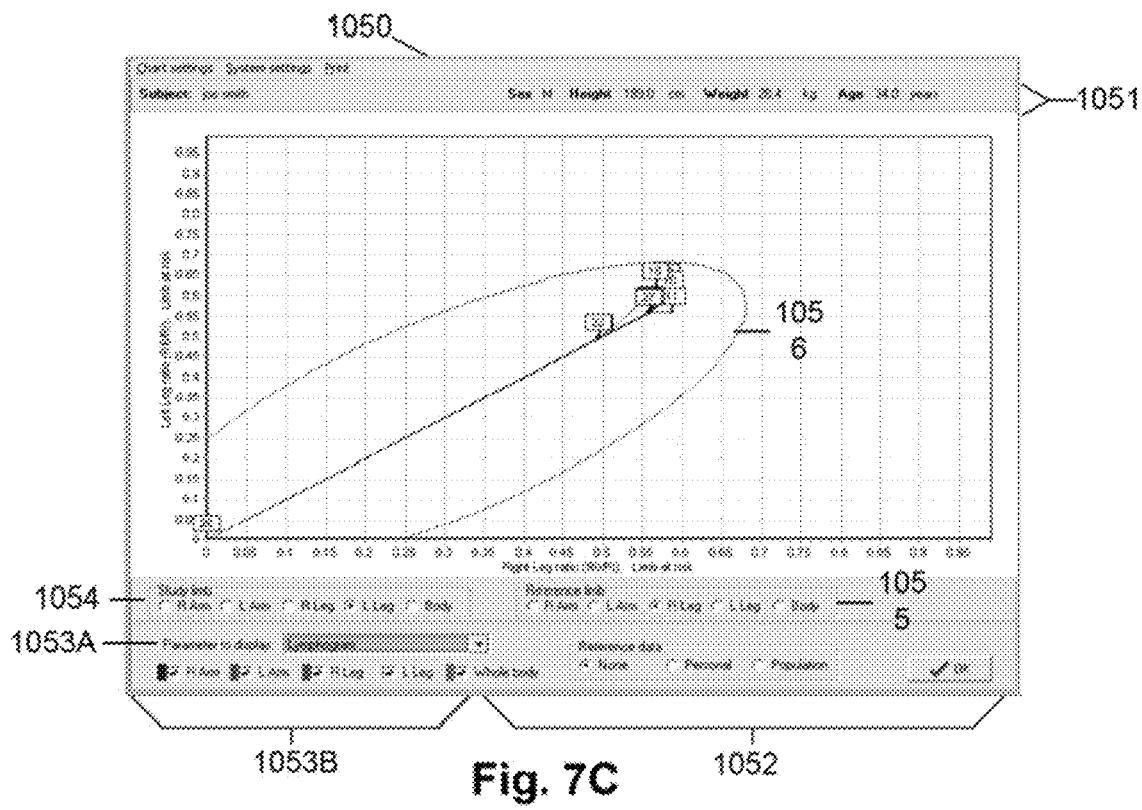
FIGS. 7C to 7I are examples of a GUI used in presenting the results of an impedance analysis.

As shown in FIG. 7C, the report is presented using a GUI 1050 that includes subject details shown generally at 1051. The GUI includes controls 1052 that allow the operator to select whether reference data is to be used and the nature of the reference data. Thus, it will be appreciated that if a user varies the reference data selection, the process will return to step 540 to reassess the nature of the output dependent on the type of reference selected. At 1053A a drop down list is provided to indicate the nature of the parameter that is to be displayed, and at 1053B checkboxes are provided indicating the limbs for which the parameter is to be displayed. In addition to this, a limb of interest and a reference limb can be selected using the check boxes 1054, 1055 as shown.

The parameters available for charting include:
Weight;
Fluid loading;
Ratio of indices;
Ratio of body segment $R_0$ values;
The index for each individual body segment $R_0$ for a body segment;
$R_\infty$ for a body segment;
The intracellular fluid resistance $R_i$;
The characteristic frequency of the subject $f_c$;
Standard error of estimates;
Td time delay for each measurement; and,
Values of $\alpha$ and $\tau$ from the Cole Model.

Each of the parameters will now be described in more detail.

Fluid Loading

The impedance vector plot is a graphical representation of when a subject's measurements move relative to a reference ellipse. The reference ellipse can be generated from a 95% confidence interval based on the subject specific baseline data or the normal population data.

When data points of a study body segment are outside the ellipse, this indicates the presence of too much fluid in the corresponding body segment. The ellipse can be generated for and displayed for each body segment chosen using the reference limb checkbox. The data points displayed are those generated from the study body segment data for the subject. The study body segments and reference body segments are chosen using the body segment selector check boxes located underneath the chart.

FIG. 7C shows an example of a fluid loading plot in which the index for left and right legs is compared. In this example, the index remains within the ellipse shown generally at 1056 highlighting that oedema is not present, and optimum dry mass has been obtained. However, when the right arm and left arm are compared as shown in FIG. 7D, the values for the ratio comparisons fall outside the reference ellipse 1056 indicating that the right arm is suffering from fluid overload and may have vascular insufficiency.

In these examples, the fluid loading plot includes a comparison between limbs, and accordingly, the checkboxes 1053B are not used.

Figure 7D:
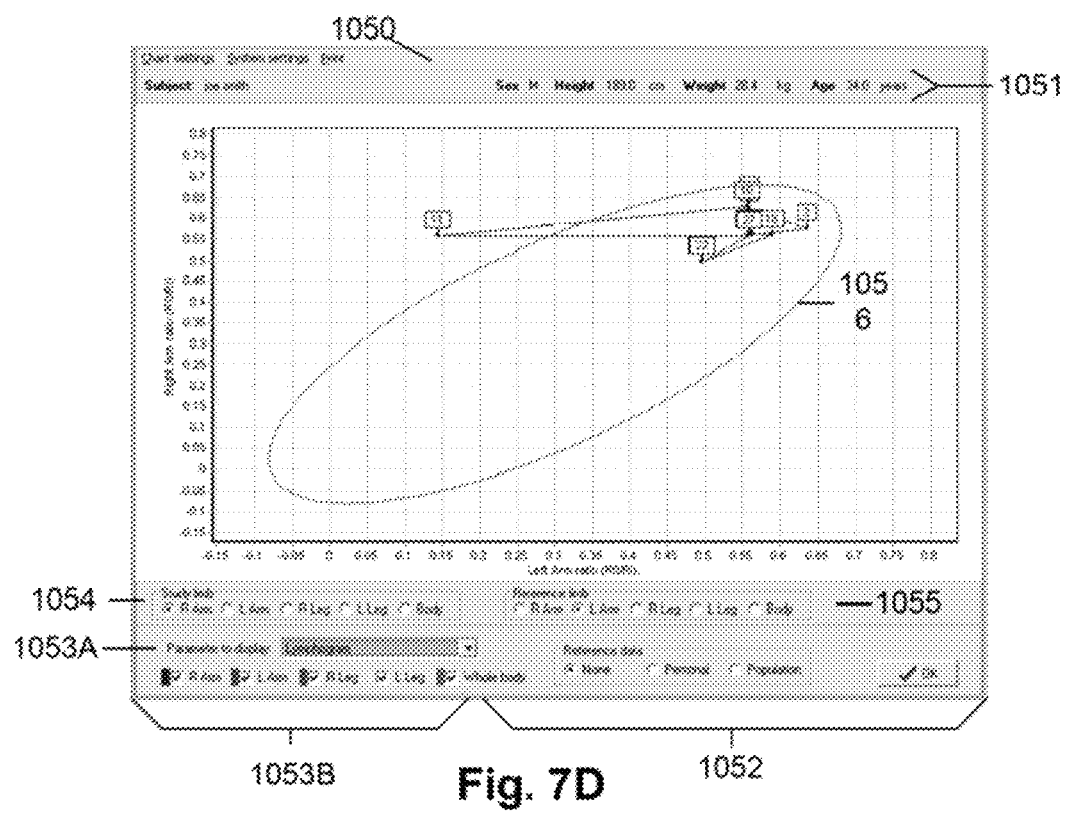
Figure 7E:
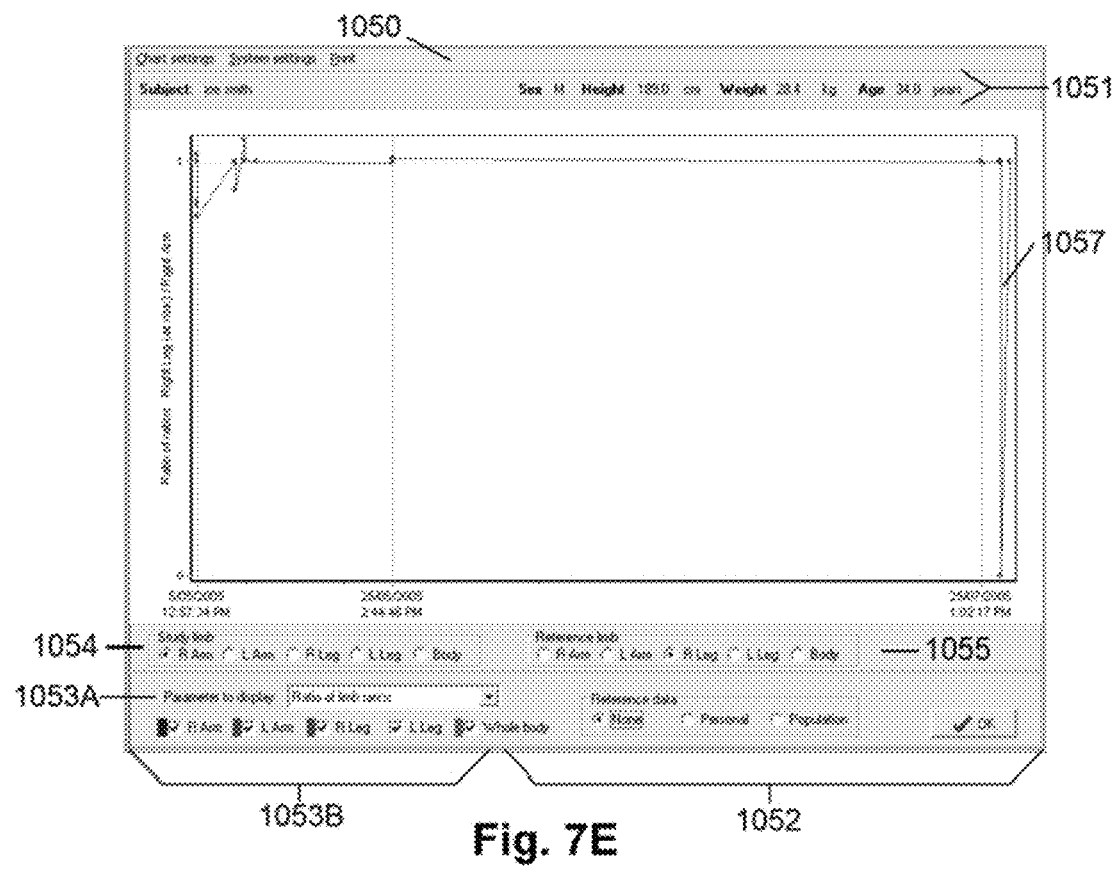
Figure 7F:
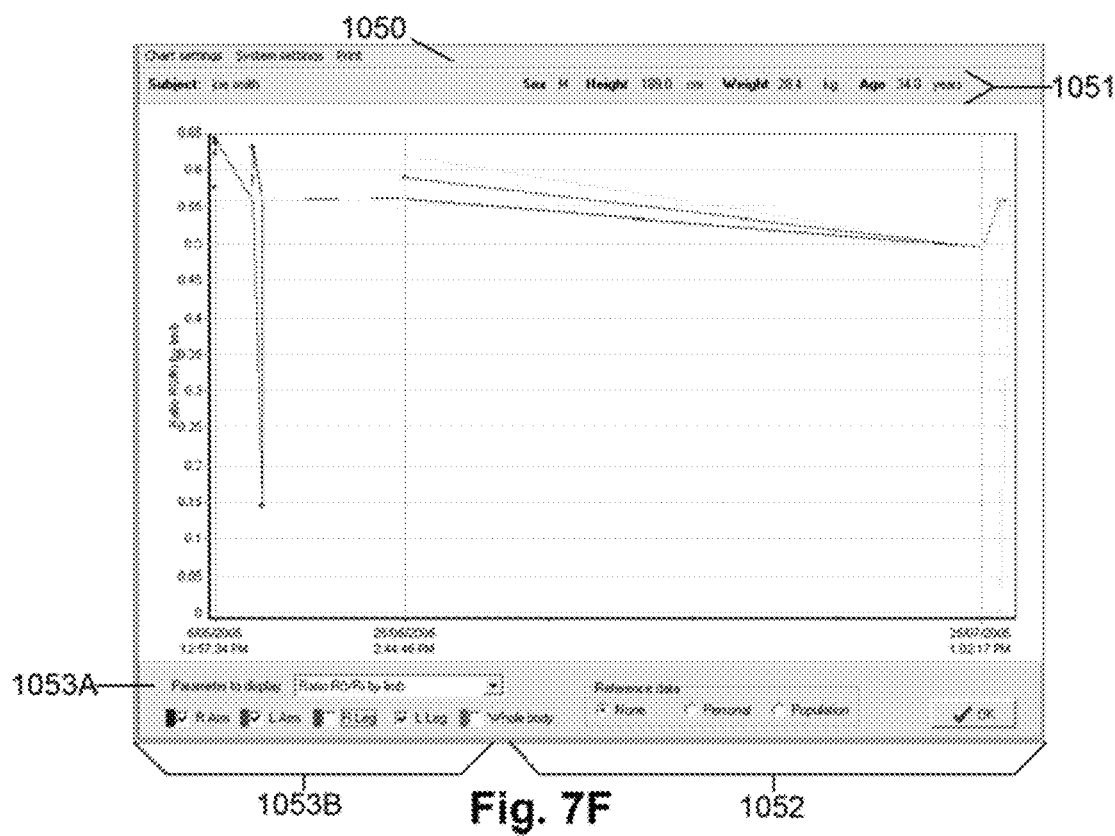
Figure 7G:
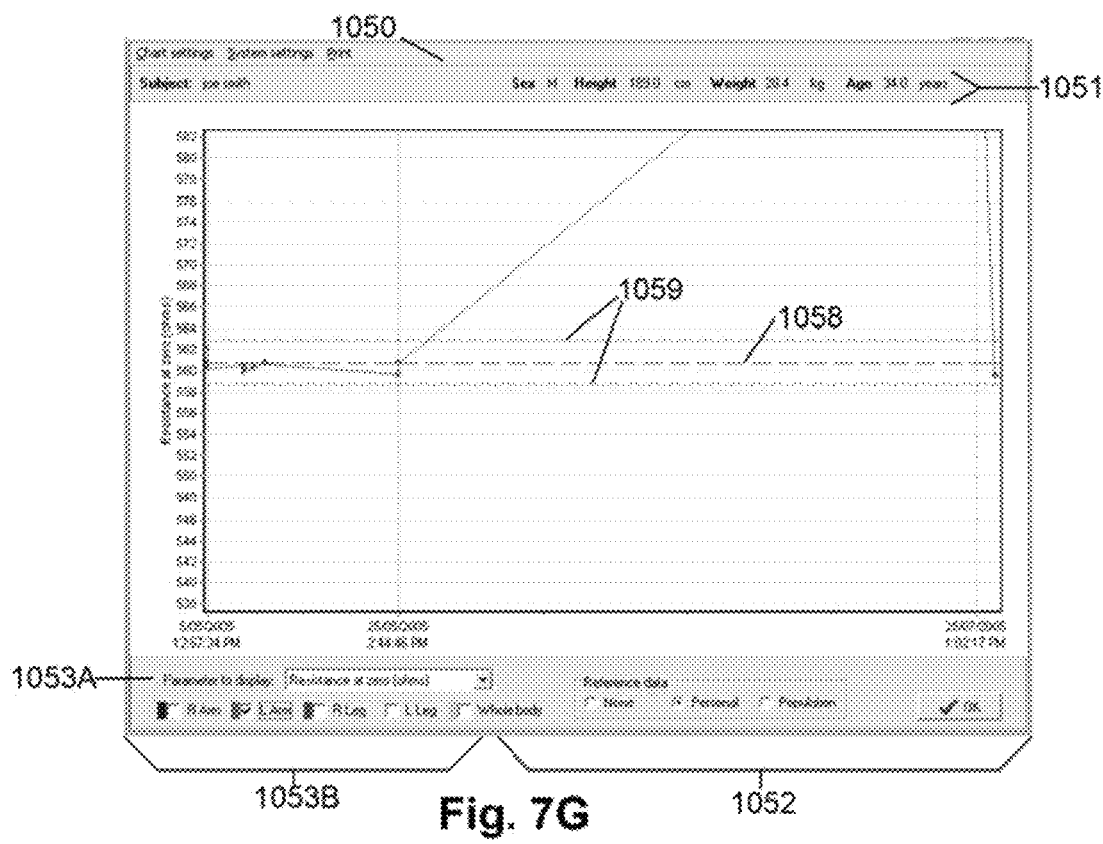
Figure 7H:
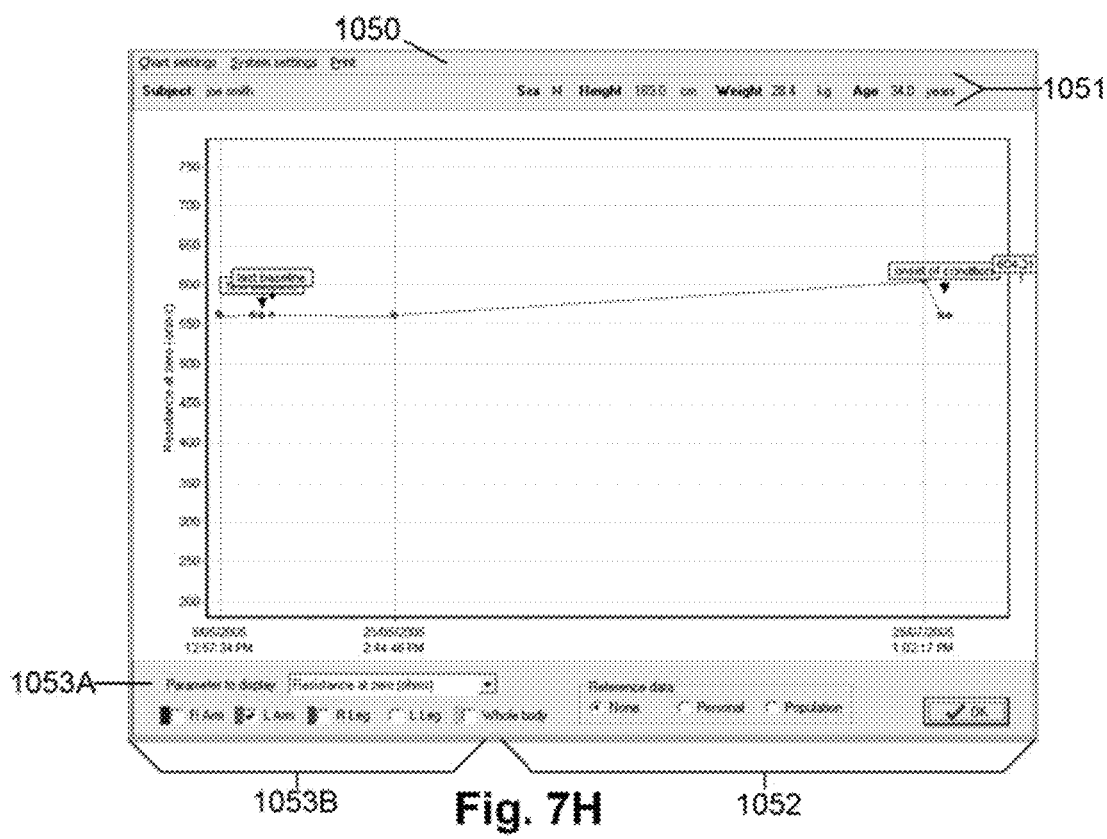
Figure 7I:
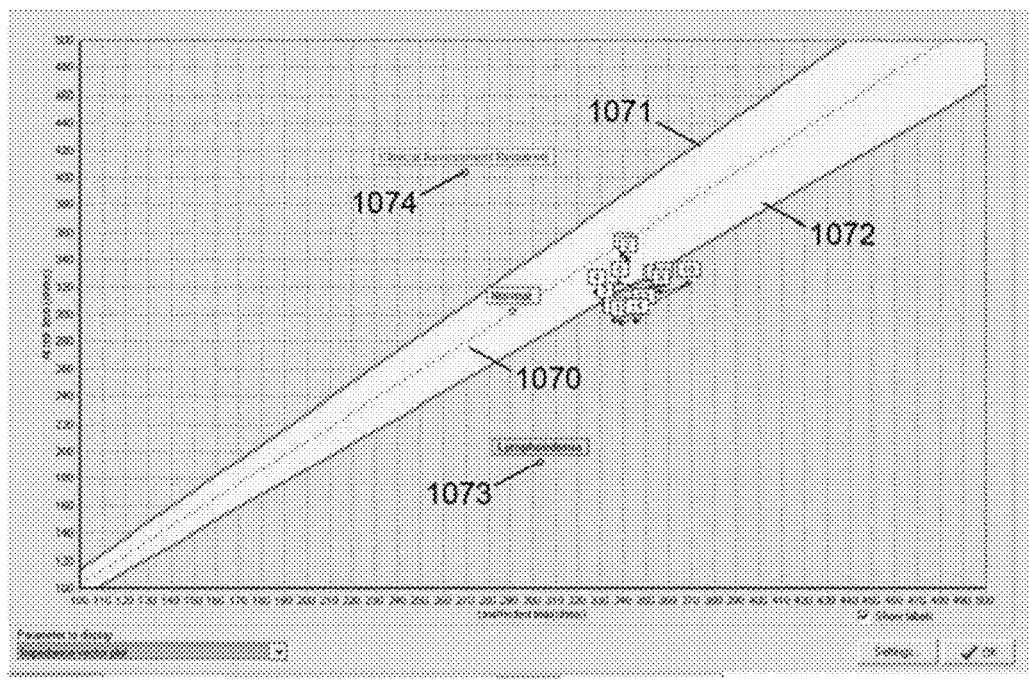

An alternative example is shown in FIG. 7I. In this example, the reference ellipse is replaced by reference lines 1071, 1072, defining a "funnel" shaped reference region 1070. In this example, the reference region may again be based on a 95% confidence interval from the subject's specific baseline data or the normal population data.

In contrast to the reference ellipse of FIGS. 7C and 7D above, the reference region 1070 is generally more able to take into account variations in physical characteristics between subjects. For example, when a reference ellipse is determined based on population samples, then if a subject has particularly thin limbs, or short fat limbs, then the subject's measured value may fall outside the ellipse, even when the hydration status is normal. However, this does not occur with the reference region 1070.

A further benefit is that if the subject has some form of oedema and is over hydrated, then this will result in the measured index value that is positioned below the reference line 1072, as shown for example at 1073.

If the measured index is determined to be above the line 1071, as shown for example at 1074, this generally indicates either that the patient is dehydrated, which will require further clinical intervention, or investigation. Alternatively, this indicates that the electrodes have been incorrectly attached to the subject, in which case re-measurement may be required.

Ratio of Body Segment Indices

This will display the index I for a selected reference limb divided by the index I of the limb of interest.

FIG. 7E is an example of the ratio of limb ratios in which a ratio of the index for the right arm and right legs is plotted against time. In this instance, it can be seen that a significant variation is present at 1057 indicating an undesirable fluid loading.

In this examples, as two limbs are again compared, the checkboxes 1053B are not used, and are ignored.

Ratio of Body Segments $R_0$ Values

This function will display the ratio of the $R_0$ of the reference body segment divided by that of a study body segment for each measurement in the subject's database table.

Index I for Each Body Segment

The index I can also be displayed for each body segment for all measurements in the subjects database table as a chart over time, as shown in FIG. 7F. The body segments represented on the chart are selected using the control 1053. In this instance, as reference and study limbs are not defined, the 1054, 1055 are omitted for clarity.

Resistance at Zero kHz ($R_0$) for a Single Body Segment

The value of $R_0$ can also displayed for each body segment for all measurements in the subjects database table as a chart over time.

Resistance at Infinite Frequency ($R\infty$) for a Single Body Segment

The value of $R_\infty$ can also displayed for each body segment for all measurements in the subjects database table as a chart over time.

Resistance for the Intracellular Fluid ($R_i$) for a Single Body Segment

The value of $R_i$ can also displayed for each body segment for all measurements in the subjects database table as a chart over time.

Characteristic Frequency for Single Body Segment

The characteristic frequency can also displayed for each body segment for all measurements in the subjects database table as a chart over time.

Value of $\alpha$ and $\tau$ from the Cole Model

The value of $\alpha$ and $\tau$ can also displayed for each body segment for all measurements in the subject's database table as a chart over time.

SEE (Standard Estimate Of Errors) Values for a Single Body Segment

The value of the standard estimate of errors (SEE) can also displayed for each body segment for all measurements in the subjects database table as a chart over time.

Td (Time Delay) Values for a Single Body Segment

The value of the time delay (Td) associated with each measurement can also displayed for each body segment for all measurements in the subjects database table as a chart over time.

Reference Indications

In each of the above outlined reports, reference values can also be displayed based either on the normalised population reference or subject specific reference.

An example of the use of a subject's specific reference value is shown in FIG. 7F. In this instance the reference value is based on $R_0$ as shown at 1058. Accordingly, it can be seen that variation of the value $R_0$ compared to the reference is indicative of oedema. The generation of a report by comparison to normal population data will be performed in a similar manner.

In addition to simply displaying the absolute reference value determined, it is also possible to display standard deviations as shown at 1059 to thereby provide an indication of the degree of variation from the base line.

Event Markers

A further feature of the process is the ability to associate event markers with specific measurements in the measurement database table. Event markers can provide commented time points that correspond to measurements and points in time. These can be customised by the user to indicate important events that need to be documented on the longitudinal analysis charts. Such events may include, onset date of oedema, the start of medical intervention, the beginning and end of dialysis sessions etc. These markers will be displayed automatically on the longitudinal charts that are a function over time. Event markers can also be shown on charts as shown for example in FIG. 7H.

Alternative Analysis

In the above examples, the processing system 10 therefore selects the types of analysis or representation that is most appropriate for determining the presence or absence of oedema based on the currently available data. This therefore removes the requirement for the operator to make an assessment of which form of report would provide the most accurate indication of the onset of oedema.

In the above example, the impedance measurements are collected for each of the limbs, with the assessment of the preferred type of analysis being performed after the measurements have been performed. However, as an alternative to this, the processing system 10 can be adapted to determine the preferred type of analysis first and then only perform the measurements required in order for the type of analysis to be performed.

Thus a limited limb analysis can be performed, in which the operator specifies the limbs for which measurements are to be made prior to the measurement process. In this instance, data will only be collected for the limbs of interest.

In addition to performing the measurements described above, it is possible that profiles can be configured to allow a range of different measurements to be performed.

For example, the TBW can be used in:
body composition analysis
derivation of Fat Free Mass (FFM), which can in turn be used as an index of left ventricular mass;
monitoring the build up of fluid in the body of cardiac patients, which can be used as an indicator of right ventricular failure.

Furthermore, by subtracting measured impedance values obtained for each limb from the corresponding impedance values obtained for the entire body, this can be used to derive effective thoracic cavity impedance values. These values can in turn be used as indicators for pulmonary oedema, and hence left ventricular failure, as well as determining cardiac output.

Thus, it will be appreciated that in addition to measuring hydration status, different measurement profiles can be determined to allow measurement of:

Cardiac parameters;
Pulmonary oedema;
Lymphoedema;
Body composition; and,
Total body water.

Remote Computer System

Figure 9:
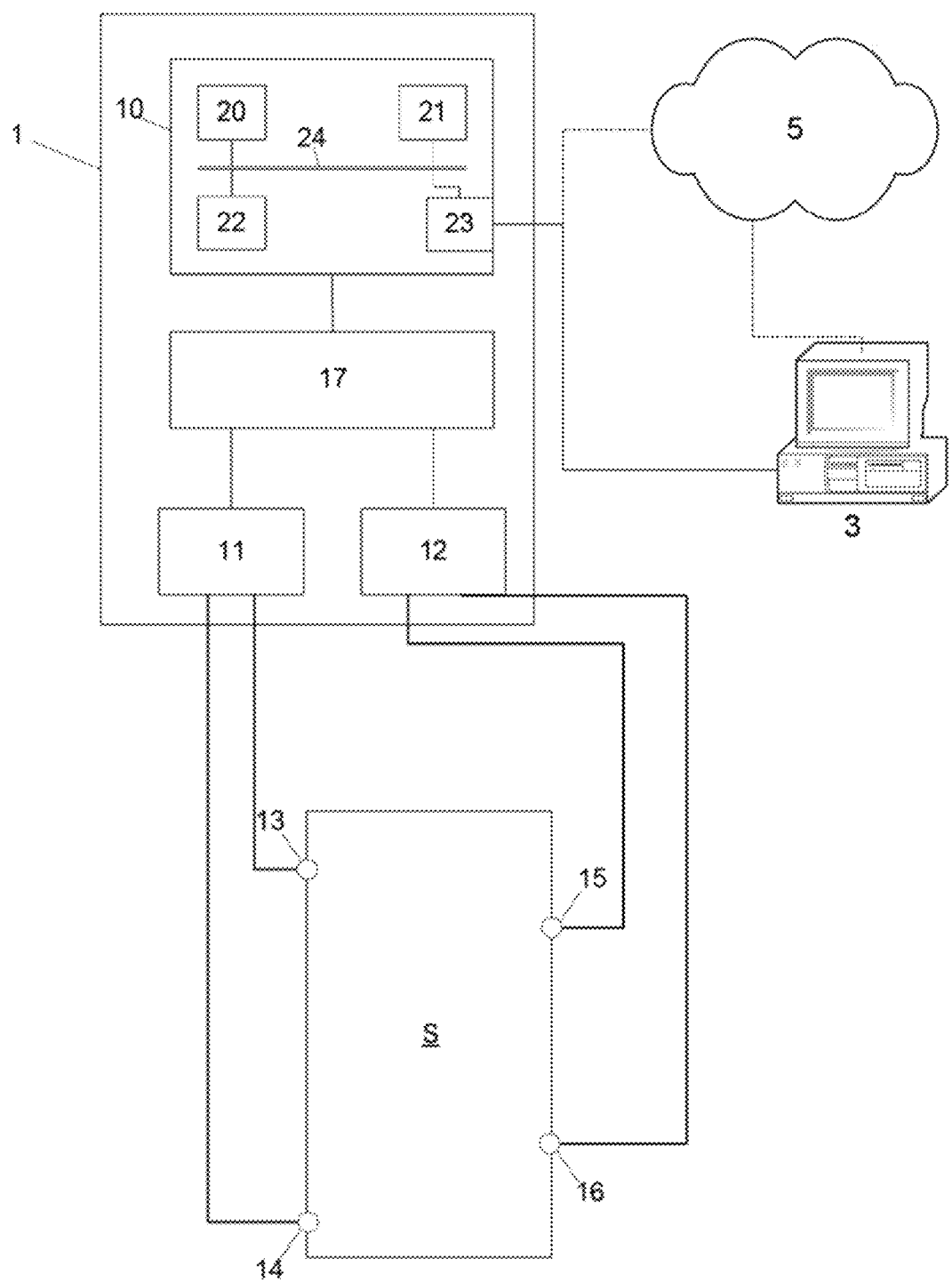
FIG. 9 is a schematic of a second example of impedance determination apparatus; and, FIG. 10 is a schematic of a GUI used in configuring the apparatus of FIG. 9.

The above examples have been described on the basis of the selection of the preferred impedance measurements and analysis being performed by a processing system 10 provided as part of the measuring device. However, this is not essential and that any or all of the functionality described could be performed by a processing system that is remotely located to the measuring device, as will now be described with respect to FIG. 9.

In this example, the measuring device 1 (which is shown as a single channel device for clarity purposes only) is connected to a computer system 3, via the external interface 23 as shown. The computer system 3 may be any form of computer system but is typically a desktop, laptop, tablet, PDA, Smart Phone or the like.

In this example, the computer system 3 operates to control the measuring device 1 to perform the measurement procedure. The measuring device 1 therefore operates to generate required excitation signals, apply these to the subject, and measure the resulting voltages generated across the subject. Once impedance measurements have been collected, these are transferred via the external interface 23 to the end station 3, which operates to analyse the measured impedance values and generate the appropriate GUIs shown in FIGS. 5 to 8.

In order to achieve this, the computer system 3 may be connected to the measuring device 1 via a wired, or wireless connection, or alternatively via an appropriate communications network 5, such as an Ethernet, LAN, WAN, the Internet, or the like.

In this instance, the operator of the system is generally required to place the measuring device 1 in a predetermined operating mode allowing the computer system 3 to generate any required control signals to activate the measurement process.

Figure 10:
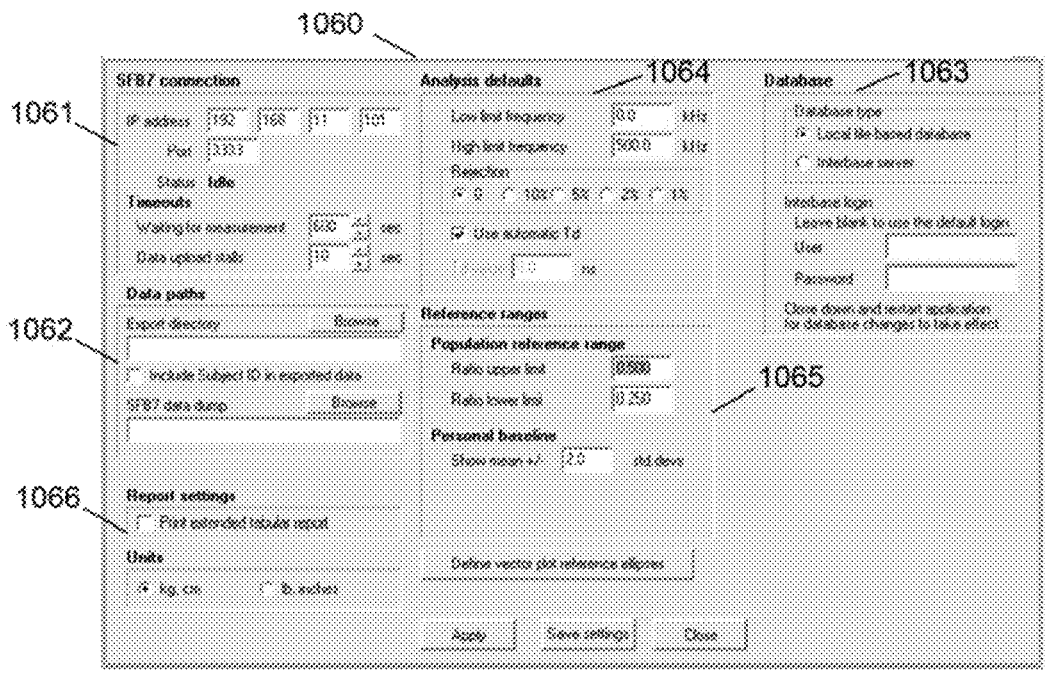

In this example, communication between the computer system 3 and the measuring device 1 is typically controlled using the GUI 1060 shown in FIG. 10.

The GUI includes fields 1061 for defining IP connection details, which allows the computer system 3 to connect to the measuring device, via the external interface 23, via a TCP/IP or other network. Fields 1062 are used for defining paths via which the references can be obtained, with the fields 1063 defining details of the database from which the references should be obtained.

Fields 1064 and 1065 are used to define parameters relating to the impedance analysis to be performed, including default frequency, rejection and time delay limits, as well as reference ranges or the like. Finally fields 1066 are used to define properties of the resulting analysis report.

It will therefore be appreciated from this that GUI can also be used to provide connections to remote databases, such as HL7 compliant subject databases. Furthermore, the architecture can be implemented in any one of a number of manners depending on the circumstances in which the measuring device 1 is to be used.

Thus, for example, as a further alternative, the selection and/or analysis of the impedance measurements can be performed by a central base station coupled to a number of measuring devices via a suitable communications system, such as a computer network or the like. In this instance, once the base station has selected an impedance measurement type to be performed, the base station transfers an indication of this to the respective monitoring thereby causing the measuring device to display the necessary electrode connections. Once the impedance measurements have been performed, the determined measurements are returned to the base station for analysis.

Patient Orientation

It will be appreciated that the location of fluid within a subject will vary significantly as the subject moves, and in particular as the subject changes their orientation or posture.

For example, in performing dialysis it is typical for the subject to be seated in a relined position, in which case fluid is typically distributed unevenly throughout the body (and subject to any specific oedema or the like). If the subject were to stand up or lay down during the process, this results in a significant flow of fluid into or from the lower regions of the subject, such as the calf. Consequently, if measurements are made from the calf, there can be a significant variations in measured impedances associated with the subject's position.

To take this into account, the measuring device 1 may include an orientation sensor connected to the measuring device 1 as a peripheral device 4, for example. In this instance, the orientation sensor is used to derive information regarding the subject's current orientation, and this could therefore take on any one of a number of forms.

Thus, for example, the orientation sensor could be provided in a subject's bed and operate to determine the subject's orientation based on the bed configuration. Alternatively, the orientation sensor may be coupled to the subject, and in particular to the subject's leg or calf, to determine the leg or calf orientation. It will be appreciated from this that any suitable sensor may be used, and in one example, the sensor is at least partially incorporated into the electrodes 15.

In use, the measuring device 1 can modify the impedance measurement analysis based on the orientation of the subject as determined from the orientation sensor. This can again be achieved in a number of manners.

For example, if the measuring device 1 is comparing a current indication to a previous indication, such as by monitoring variations in the index I over time, the measuring device 1 can be adapted to ensure that indications are only compared to each other if made at the same subject orientation. Thus, if a preliminary impedance measurement prior to dialysis is used to establish a baseline reading, with subsequent measurements being compared thereto, the process may involve taking a baseline reading at each of a number of different orientations. In this instance, the measured readings would then be compared to the corresponding baseline determined for the same subject orientation. The fluid levels will also depend on the length of time a subject has been in a given orientation, and again this may be taken into account, for example, by ensuring comparison is made to prior readings in which the subject has maintained a similar posture for a similar amount of time.

Alternatively, by measuring different impedance values obtained over a range of orientations, this can be used to determine a correction factor, required to correct for certain orientations. This allows normalisation of any measured values to a specific orientation, allowing the above described analysis to be performed.

A further variation is to examine differences in indicators between different subject orientations. In this instance, it will be appreciated that if the subject's hydration status is such that the subject has reached an ideal or optimal fluid level, and no further dialysis is required, then changes in orientation will have a reduced effect simply because there is less fluid within the body to be displaced.

Accordingly, in a further example, the process involves determining a number of indicators at different subject orientations. The measuring device 1 then compares the measured indications at each orientation and determines if the difference falls below a threshold. If so, then this indicates that there is minimal variations in fluid between the orientations, and hence that the hydration status is suitable to terminate the dialysis procedure.

Skin Temperature

Impedances values measured for a subject include a contribution from the subject's skin, known as a skin impedance. The skin impedance is heavily influenced by the hydration levels in the skin, which is in turn dependent on skin temperature.

Accordingly, in a further example, the measuring device 1 can use the skin temperature of the subject when analysing impedance values. This can be achieved in a number of ways.

For example, the skin temperature can be measured using a suitable thermometer, with the skin temperature being supplied to the measuring device 1, via the I/O device 22. Alternatively, a skin temperature sensor can be provided as part of the measuring device, either as a peripheral device 4, or through incorporation into suitable electrodes, allowing the measuring device 1 to determine the subject's skin temperature automatically.

In this example, the skin temperature is generally used to generate a calibration factor, which is used to modify the measured impedance values, or subsequently determined indicators, depending on the skin temperature. The calibration factor is typically predetermined by analysis of a suitable sample population, across a variety of skin temperatures.

An effect of the calibration factor is that it can be used to take into account subject ethnicity. In particular, it is generally accepted that different reference baselines must be used for subjects having different ethnicities, due to variations in skin impedance. However, by providing a correction factor taking into account both ethnicity and skin temperature, allows common baselines to be used by a wider range of subjects having a wider range of ethnicities.

Electrode Arrangement

It will be appreciated that the above described electrode arrangements are only one of a number of possible electrode arrangements. For example, whilst the electrodes may be provided as discrete pads, alternatively a number of electrodes may be provided on a common substrate, for example in the case of band electrodes.

Additionally, or alternatively, the electrodes may form part of another related device. For example, the voltage measuring electrodes positioned on either the calf or bicep can be incorporated into blood pressure cuff, to allow simultaneous measurement of blood pressure and impedance.

In any event, it will be appreciated that the above described process provides an easy to use and non-invasive estimate of body composition parameters and fluid volumes. Segmental analysis provides a better estimate of these parameters then traditional whole body estimates. However the placement of electrodes in reproducible anatomic sites in the obese and the critically ill population is often impossible. By using the theory of equipotentials and sophisticated multiplexing it is possible to provide a robust bioimpedance platform capable of multiple measurement parameters for the dialysis patient.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that features from different examples above may be used interchangeably where appropriate. Furthermore, whilst the above examples have focused on a subject such as a human, it will be appreciated that the measuring device and techniques described above can be used with any animal, including but not limited to, primates, livestock, performance animals, such race horses, or the like.

It will also be appreciated above described techniques, may be implemented using devices that do not utilise the separate first processing system 10 and second processing system 17, but rather can use a common single processing system, or use some other internal configuration.

The claims defining the invention are as follows:

1. Apparatus for use in controlling dialysis, the apparatus including a processing system that:
   a) determines a plurality of measured impedance values for at least one body segment, each measured impedance value being measured at a corresponding measurement frequency;
   b) for each body segment, and by using the plurality of measured impedance values, determines at least one indicator, the indicator being at least partially indicative of a level of extracellular fluid;
   c) generates a subject specific baseline from the measured impedance values, wherein the subject specific baseline is generated by at least one of:
      i) calculating impedance measurements when the subject is healthy;
      ii) calculating impedance measurements before medical intervention; or
      iii) calculating a mean value of previous measurements;
   d) monitors a rate of change of the at least one indicator over time; and
   e) controls dialysis by selectively halting dialysis when the rate of change of the indicator falls below a predetermined threshold for at least one of the plurality of body segments and when the measured impedance values or derived indicators represent an ideal fluid level based on the subject specific baseline,
   wherein the processing system is connected to a measuring device via a wireless connection, and the processing system:
   a) causes the measuring device to perform the impedance measurements; and
   b) analyzes impedance values transferred from the receiving device.

2. Apparatus according to claim 1, wherein:
   a) the processing system:
      i) generates instructions; and
      ii) transfers the instructions to the measuring device; and
   b) the measuring device is responsive to the instructions to cause the impedance measurements to be performed.

3. Apparatus according to claim 1, wherein the processing system is connected to a dialysis machine.

4. Apparatus according to claim 1, wherein the processing system:
   a) causes one or more electrical signals to be applied to a subject using a first set of electrodes, the one or more electrical signals having a plurality of frequencies;
   b) determines an indication of electrical signals measured across a second set of electrodes applied to the subject in response to the applied one or more signals;
   c) determines from the indication and the one or more applied signals, an instantaneous impedance value at each of the plurality of frequencies; and
   d) determines the indicator using the instantaneous impedance values.

5. Apparatus according to claim 4, wherein the electrodes include:
   a) a first current supply electrode positioned on a limb being measured;
   b) a second current supply electrode on a second limb on a same lateral side of the subject as the limb being measured;
   c) a first voltage electrode positioned on a limb being measured; and
   d) a second voltage electrode positioned on a third limb contra-lateral to the limb being measured.

6. Apparatus according to claim 1, wherein the apparatus includes a measuring device including at least two channels, each channel being adapted to measure the impedance across a respective body segment, and wherein the processing system is configured to cause at least one impedance measurement to be performed using each channel.

7. Apparatus according to claim 1, wherein the processing system determines the parameter values using equation:

$$Z = R_\infty + \frac{R_0 - R_\infty}{1 + (j\omega\tau)^{(1-\alpha)}}$$

where:
   $Z$ is the measured impedance at angular frequency $\omega$,
   $\tau$ is a time constant, and
   $\alpha$ has a value between 0 and 1.

8. Apparatus according to claim 1, wherein the indicator for a body segment is the extracellular fluid volume determined using equation:

$$ECV_{Segment} = C_{Segment} \rho_{Segment} \left( \frac{L^2_{Segment}}{R_{Segment}} \right)$$

where:
   ECV=Extracellular fluid volume,
   $C_{segment}$=Geometry Constant which is 1 for an arm or leg and 4 for the thoracic cavity,
   $L_{segment}$=Length of the segment in cm,
   $R_{segment}$=Resistance of the segment in Ohm, and
   $P_{segment}$=Resistivity coefficient which is nominally 47 Ohm/cm.

9. Apparatus according to claim 1, wherein the at least one body segment includes at least one of:
   a) a limb;
   b) a calf; or
   c) a bicep.

10. Apparatus according to claim 1, wherein the processing system:
   d) determines a first indicator at a first time;
   e) determines a second indicator at a second time; and
   f) determines the rate of change using the difference between the first and second indicators and the first and second times.

11. An apparatus according to claim 1, wherein the processing system displays an indication of at least one of:
   a) at least one measured impedance value;
   b) a hydration status;
   c) parameter values;
   d) the indicator;
   e) an extracellular fluid volume; or
   f) a ratio of extracellular to intracellular fluid.

12. Apparatus according to claim 1, wherein the subject specific baseline is generated by at least one of:
   a) calculating one or more impedance values; or
   b) retrieving from a condition database.

13. Apparatus according to claim 1, wherein the subject specific baseline is generated by calculating the mean value of previous measurements.

14. Apparatus according to claim 1, wherein the subject specific baseline is generated by calculating impedance measurements when the subject is healthy.

15. A method of controlling dialysis of a subject, the method including, in a processing system:
   a) determining a plurality of measured impedance values for at least one body segment;
   b) for each body segment, and using the measured impedance values, determining at least one indicator, the indicator being at least partially indicative of a level of extracellular fluid;
   c) generating a subject specific baseline from the measured impedance values, wherein the subject specific baseline is generated by at least one of:
      i) calculating impedance measurements when the subject is healthy;
      ii) calculating impedance measurements before medical intervention; or
      iii) calculating a mean value of previous measurements;
   d) monitoring a rate of change of the at least one indicator over time; and
   e) controlling dialysis by selectively halting dialysis when the rate of change of the indicator falls below a predetermined threshold for at least one of the plurality of body segments and when the measured impedance values or derived indicators represent an ideal fluid level based on the subject specific baseline,
   wherein the processing system is connected to a measuring device via a wireless connection, and wherein the method further includes, by the processing system:
   a) causing the measuring device to perform the impedance measurements; and
   b) analyzing impedance values transferred from the receiving device.

16. Method according to claim 15, wherein the subject specific baseline is generated by at least one of:
   a) calculating one or more impedance values; or
   b) retrieving from a condition database.

* * * * *